US011255761B2

(12) United States Patent
Smith et al.

(10) Patent No.: US 11,255,761 B2
(45) Date of Patent: *Feb. 22, 2022

(54) METHOD OF ANALYSING A CELL OR OTHER BIOLOGICAL MATERIAL CONTAINING A NUCLEIC ACID

(71) Applicant: Biostatus Limited, Leicestershire (GB)

(72) Inventors: Paul James Smith, Vale of Glamorgan (GB); Rachel J. Errington, Leicestershire (GB); Laurence Hylton Patterson, Leicestershire (GB)

(73) Assignee: Biostatus Limited, Shepshed (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/731,647

(22) Filed: Jun. 5, 2015

(65) Prior Publication Data
US 2015/0268142 A1    Sep. 24, 2015

Related U.S. Application Data

(62) Division of application No. 13/639,872, filed as application No. PCT/GB2011/050702 on Apr. 8, 2011, now Pat. No. 9,051,467.

(30) Foreign Application Priority Data

Apr. 9, 2010 (GB) .................................. 1005939.2

(51) Int. Cl.
| C12Q 1/68 | (2018.01) |
| G01N 1/30 | (2006.01) |
| G01N 33/48 | (2006.01) |
| G01N 33/567 | (2006.01) |
| C09K 11/06 | (2006.01) |
| C09B 1/16 | (2006.01) |
| C09B 1/20 | (2006.01) |
| G01N 33/58 | (2006.01) |
| A61K 31/54 | (2006.01) |

(52) U.S. Cl.
CPC ................. G01N 1/30 (2013.01); C09B 1/16 (2013.01); C09B 1/207 (2013.01); C09K 11/06 (2013.01); C12Q 1/68 (2013.01); G01N 33/582 (2013.01); C09K 2211/1011 (2013.01); G01N 2001/302 (2013.01)

(58) Field of Classification Search
CPC .............. G01N 1/30; C09B 1/16; C12Q 1/68
See application file for complete search history.

(56) References Cited

U.S. PATENT DOCUMENTS

| 3,123,605 | A | * | 3/1964 | Turetzky et al. ....... C09B 1/002 |
| | | | | 544/156 |
| 3,442,895 | A | | 5/1969 | Bugaut |
| 3,467,483 | A | * | 9/1969 | Gregoire ................ A61K 8/355 |
| | | | | 544/156 |
| 3,646,072 | A | | 2/1972 | James |
| 4,123,222 | A | | 10/1978 | Loew |
| 4,421,859 | A | * | 12/1983 | Bore .................. G01N 33/5091 |
| | | | | 436/119 |
| 2003/0008316 | A1 | | 1/2003 | Smith et al. |
| 2007/0082377 | A1 | | 4/2007 | Olin et al. |
| 2010/0062429 | A1 | * | 3/2010 | Patton .................. C07C 225/34 |
| | | | | 435/6.1 |

FOREIGN PATENT DOCUMENTS

| EP | 0758547 | 8/2001 |
| FR | 1379649 | 11/1964 |
| GB | 939513 | 10/1963 |
| GB | 2027195 | 7/1980 |
| JP | 50003337 | 2/1975 |
| JP | 52114784 | 9/1977 |
| JP | 04136802 | 5/1992 |
| JP | 09118832 | 5/1997 |
| JP | H09-118832 | 5/1997 |
| JP | S52-114784 | 9/1997 |

(Continued)

OTHER PUBLICATIONS

Biggerstaff, et al., "New methodology for viability testing in environmental samples", Mol Cell Probes, 20:141-6 (2006).
Katzhendler, et al., "Synthesis of aminoanthraquinone derivatives and their in vitro evaluation as potential anti-cancer drugs", Eur J Med Chem., 24:23-30 (1989).
Luxami, et al., "Quaternary ammonium salt-based chromogenic and fluorescent chemosensors for fluoride ions", Tetrahedron Lttrs, 49:4265-8 (2008).
Murdock, et al., "Antitumor agents. 1. 1,4-Bis[(aminoalkyl)amino]-9,10-anthracenediones", J Med Chem., 22(9):1024-30 (1979).
Nanayakkara, et al., "synthesis of water-soluble 9, 10-anthraquinone analogues with potent cyanobacterial activity toward the musty-odor cyanobacterium oscillatoria peromata", J Agric Food Chem., 56:1002-7 (2008).
Japanese Examination report for JP 2013-503178 dated Feb. 23, 2015.
English Translation of Japanese Examination Report for JP 2016-209377, dated Sep. 28, 2017.

(Continued)

Primary Examiner — Barbara P Badio
(74) Attorney, Agent, or Firm — Evan Law Group LLC

(57) ABSTRACT

According to the invention there is provided a compound of Formula (I) in which: A is a $C_{2-8}$ alkylene group; $R^1$, $R^2$, $R^3$, and $R^4$ are independently selected from hydrogen, $C_{1-4}$ alkyl, $C_{2-4}$ dihydroxyalkyl in which the carbon atom attached to the nitrogen atom does not carry a hydroxyl group and no carbon atom is substituted by two hydroxyl groups, or $R^2$ and $R^3$ together form a $C_{2-6}$ alkylene group which with the nitrogen atom to which $R^2$ and $R^3$ are attached forms a heterocyclic ring; $X_1$, $X_2$ and $X_3$ are independently selected from hydrogen, hydroxyl, $NR^1$-A-$NR^2R^3R^4+(Z^{m-})_{1/m}$, for halogeno amino, $C_{1-4}$ alkoxy or $C_{2-8}$ alkanoyloxy; and $(Z^{m-})_{1/m}$ is an anion of charge m; or a derivative in which the group $NR^1$ is quaternarized.

17 Claims, 12 Drawing Sheets

(56) References Cited

FOREIGN PATENT DOCUMENTS

| | | |
|---|---|---|
| JP | 2002-531587 | 9/2002 |
| JP | 2002539259 | 11/2002 |
| WO | 99065992 | 12/1999 |
| WO | 2000056333 | 9/2000 |
| WO | 2004060061 | 7/2004 |

OTHER PUBLICATIONS

JP 2016-209377 DIV 2nd Office Action (English translation) dated Sep. 10, 2018.
Ichikawa, et al., "1-amino-substituted-, and 1,5- and 1,8-bis(amino-substituted) oxyanthraquinone-based cationic dye synthesis", Kogyo Kagaku Zashi, 67(1)142-5 (1964b) (with concise explanation of relevance).
Ichikawa, et al., "1,4-bis(amino-substituted)- and 1-(amino-substituted)-4-oxyanthraquinone-based cationic dye synthesis", Kogyo Kagaku Zashi, 67(1):138-42 (1964a) (with concise explanation of relevance).
Office Action—First Examination Report (English translation) Brazilian Application No. BR112012025820-6, dated Jun. 5, 2018.
Office Action—First Examination Report (English translation) Indian Application No. 9321/CHENP/2012 dated Jan. 30, 2018.
Office Action—First Examination Report (English translation) Korean Application No. 10-2018-7009266 dated Sep. 1, 2018.
Search Report—European Application No. 18167949.9 dated May 28, 2018.

\* cited by examiner

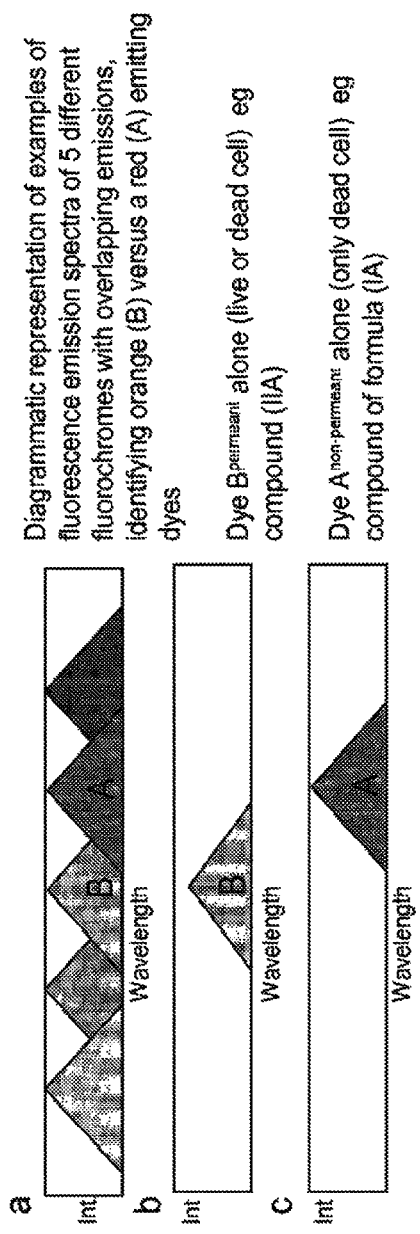
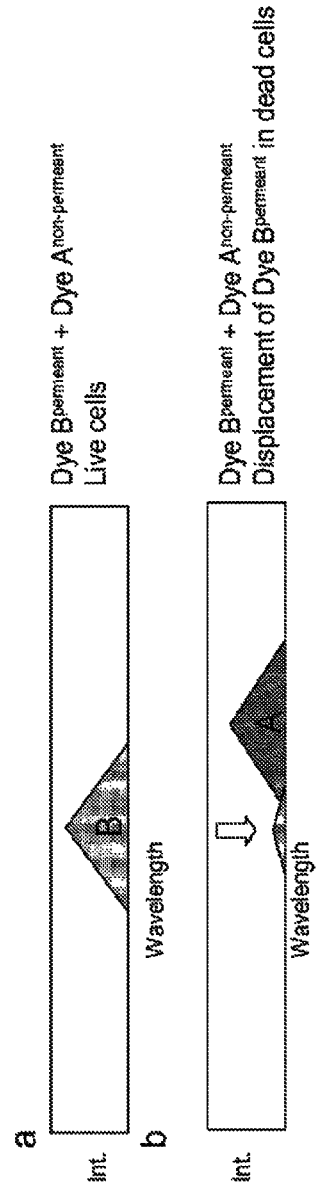

Diagrammatic representation of a dot plot indicating the staining characteristics of groups of cells and their defined characteristics using a dual analysis of compound of formula (IA) staining versus fluorescently labelled (eg FITC) Annexin V staining

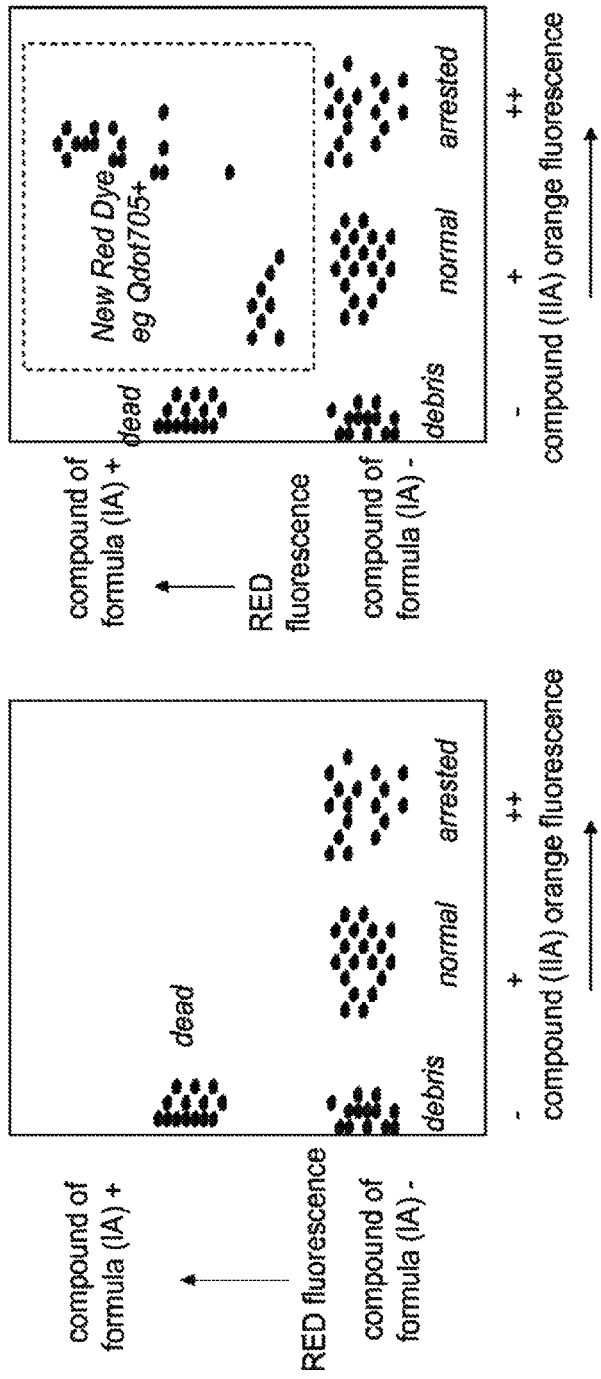

Diagrammatic representation of a 3D dot plot indicating the staining characteristics of groups of cells and examples of their defined characteristics using a triple analysis of staining with compound of formula (IA) versus compound (IIA) versus Annexin V binding, and the potential for further multicolour analyses

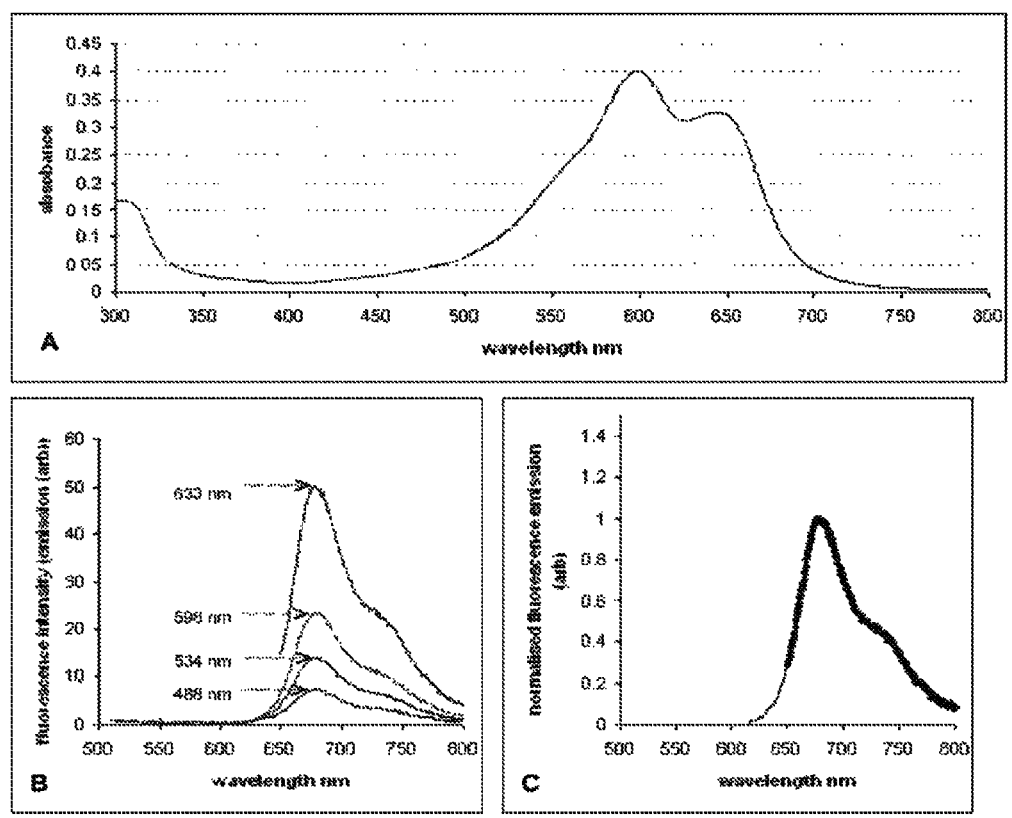
Figure 8: Spectral Properties of compound of Formula (IA)

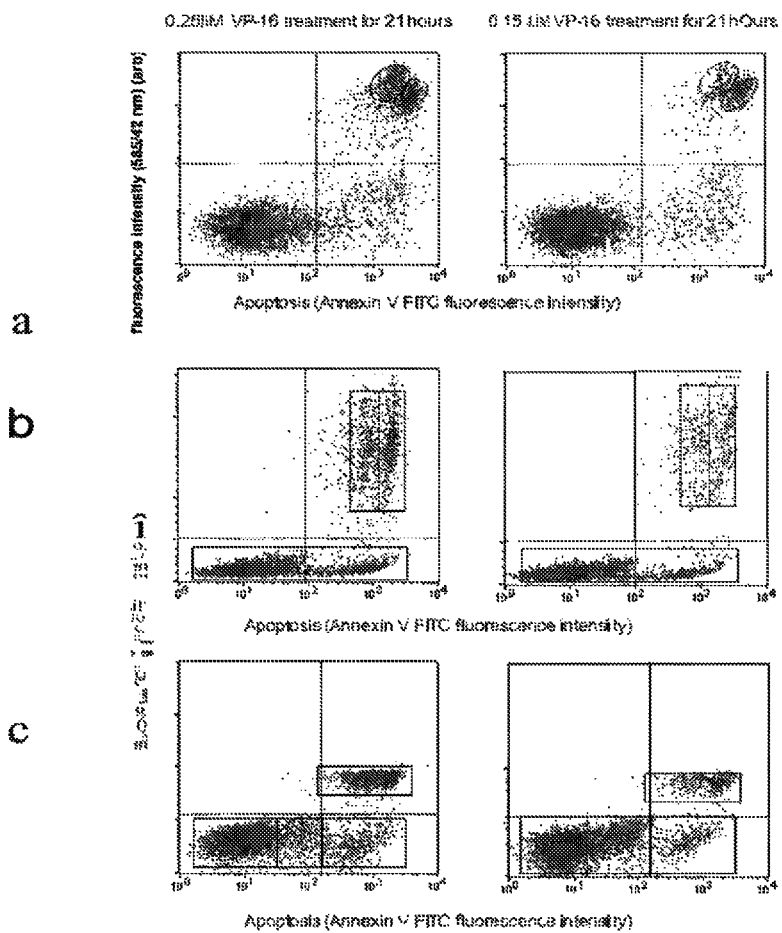

Figure 9: shows fluorescence obtained from experiments using Annexin V-FITC in combination with (a) propidium iodide (PI) with PI fluorescence intensity on a log scale, (b) a compound of Formula (IA), with compound of Formula (IA) fluorescence intensity shown on a linear scale, (c) a compound of Formula (IA), with a compound of Formula (IA) fluorescence intensity shown on a log scale;

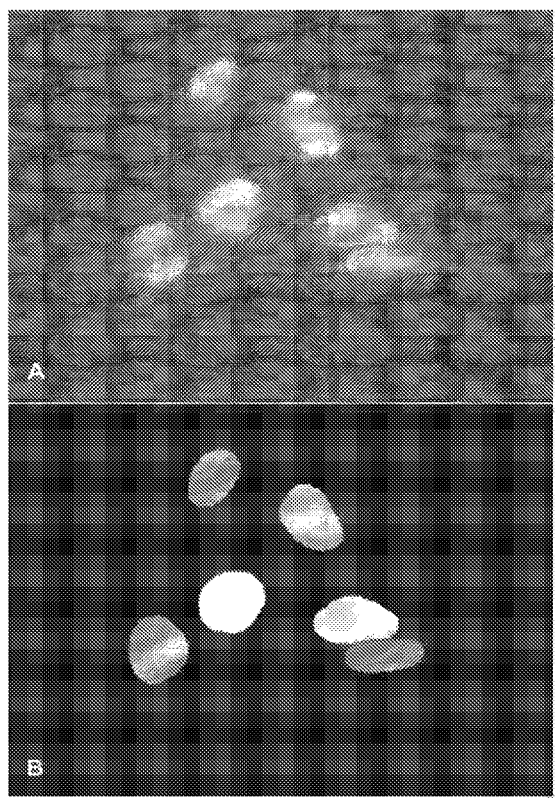
Figure 10: Prominent nuclear staining of fixed U-2 OS human osteosarcoma cells using compound described by Formula (IA)

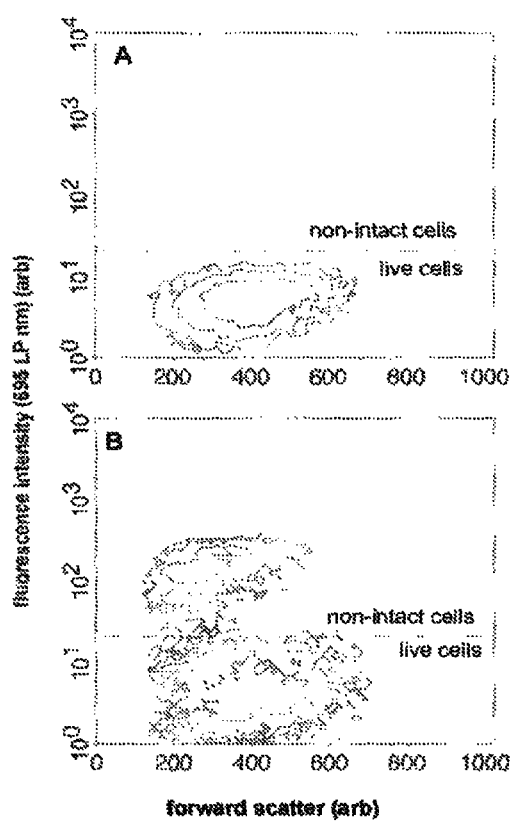
Figure 11: The staining of cells with compromised membranes using compound described by Formula (IA)

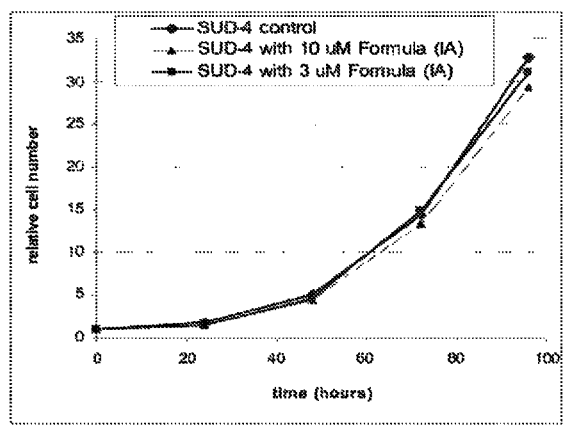
Figure 12: The effect of incubation of human B cell lymphoma (SU-DHL-4) cells with a compound of Formula (IA) revealing the low toxicity

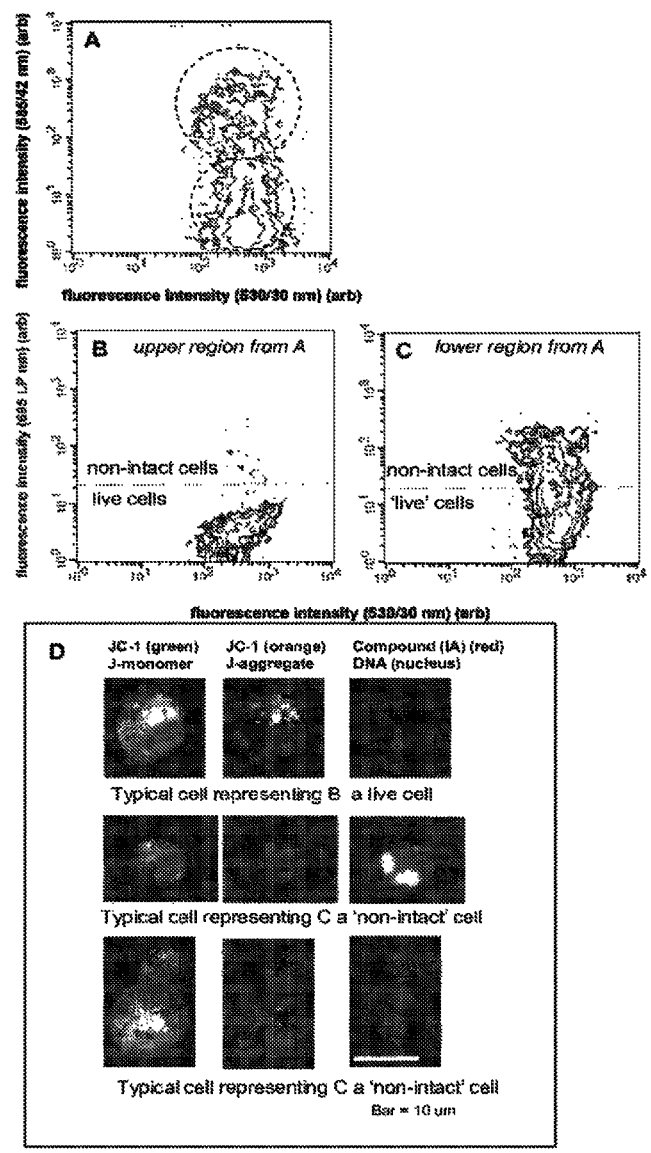
Figure 13: Early stage in human Jurkat cell death associated with the loss of mitochondrial membrane potential and plasma membrane integrity in response to the apoptosis inducing agent staurosporine.

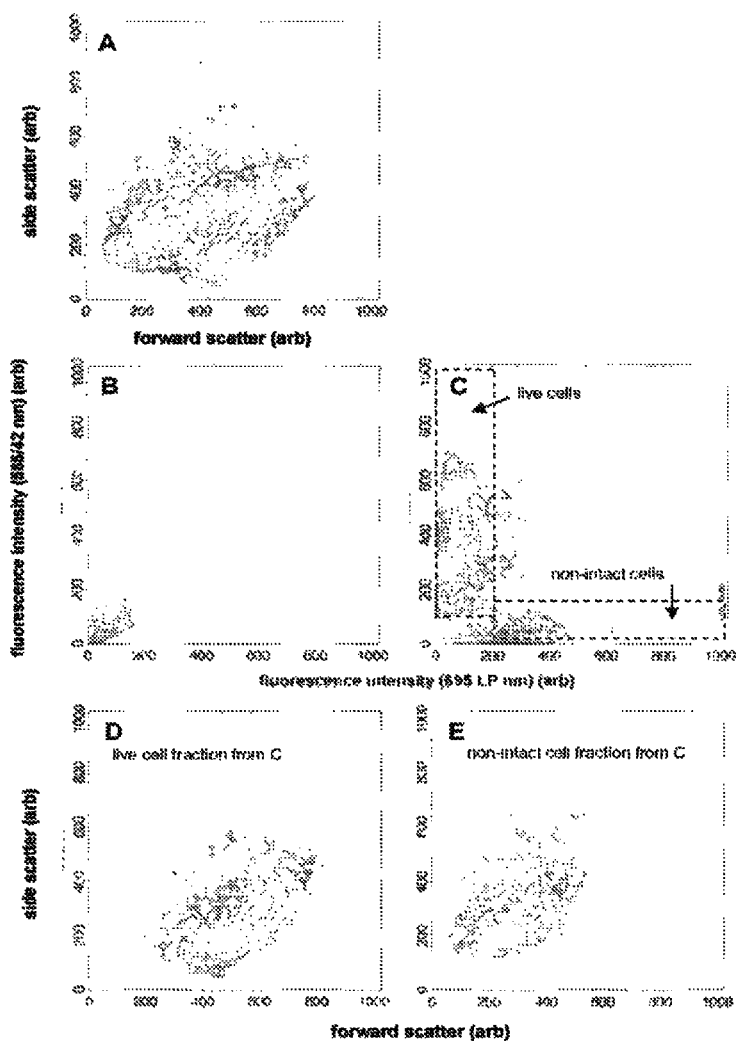
Figure 14: Combination tracking of cell status using co-targeted fluorescent probes compound (IA) (dead cells) and compound (IIA) (live cells).

METHOD OF ANALYSING A CELL OR OTHER BIOLOGICAL MATERIAL CONTAINING A NUCLEIC ACID

This invention relates to a method of analysing a cell or other biological material, methods of discriminating between intact and non-intact cells, detection systems for same, and also to certain novel compounds and to fluorescent complexes including these compounds and a nucleic acid. The invention has wide ranging applications in the analysis of cells and other biological material, with particular, although not exclusive, reference to a class of cell impermeant fluorescent dyes and their uses.

Methods for the determination of the cell concentration and viability of specimens, including the discrimination of cellular integrity in non-fixed cell samples and the staining of nucleic material in fixed and permeabilised cell samples, are in common use in the life sciences and in the health care industries.

The ability to identify processes associated with morphological, biochemical, and molecular changes which predispose, precede, and accompany cell death (eg necrosis or apoptosis) is of widespread interest in the life sciences. Molecular probe technologies, readily deployed on flow cytometry and microscopy platforms, that allow cellular level study of such processes in cell samples not subjected to prior fixation are particularly attractive (Darzynkiewicz, Juan et al. 1997). Several fluorescent dye-based staining protocols have been developed for flow cytometric and microscopical analysis of eukaryotic cell and bacterial viability.

Live versus dead cell analyses have previously exploited the ability of an intact or metabolically active cell to exclude the penetration of colorimetric or fluorescent dyes into one or more cellular compartments. In higher, eukaryotes this property primarily relates to the integrity of the plasma membrane, whereas in lower eukaryotes, prokaryotic systems and plants, cell wall composition and disruption can also affect dye penetration and behaviour. The transition phases from live to dead cell states have been described but frequently differ between cells of different types and in the rapidity and forms of the processes involved. Live, intact or viable cells are understood to be those that retain both a degree of metabolic function and integrity of the plasma membrane without necessarily implying proliferative capacity. The loss of plasma membrane integrity, rather than other processes of membrane reorganisation, is a critical point in the cell death process and results in the potential for cells to show the enhanced or freer passage of molecules, according to their specific properties, between the internal environment and the external environs of the cell. An example of membrane reorganisation during cell death is given by the enhanced binding of Annexin V molecules to the cell surface but needs to be distinguished from the binding of Annexin V to cells with disrupted membranes representing a later stage in cell death associated with positive staining by a cell impermeant dye.

Cells displaying compromised membrane integrity can foe described as non-viable or non-intact cells and are understood to include dead, permeabilised or dying cells showing features of membrane disruption. This critical transition point can be identified by the enhanced entry of live cell impermeant dyes providing a functional definition of cell death and a method of analysis. Preferably such dyes would have the capacity to bind to residual intracellular structure and therefore preferentially accumulate within the non-intact fraction of cells within a population. It is understood that there is a relatively long term retention of residual nucleic add bearing structures during cell death and the eventual disassembly of the cell unit into multiple fragments frequently identified as debris.

Vital stains can be used to detect, and therefore select, a population of cells. This is particularly advantageous in assays that require retention of the functionality of live, non-compromised cells. One approach is to positively assess viability by the detection of active cell metabolism which can be determined by the intracellular conversion of a cell permeant non-fluorescent substrate into a highly fluorescent product that is preferentially retained within an intact cells (e.g. fluorescein diacetate metabolism by intracellular non-specific esterase activity) thereby positively identifying a viable fraction. In such cases the exclusion of cells with compromised integrity acts to enhance the validity of the information derived from the assay. On the other hand, live cell-impermeant stains will enter membrane-compromised cells that are dead or are in later stages of apoptosis or cell death. In the case of cell impermeant DNA binding dyes, dye entry and subsequent interactions with intracellular residual nucleic acids is used to report the compromised status of the membrane of a given cell. In such cases the 'complex' between the intracellular dye and the residual nucleic acids, preferably DNA, is the reporting principle. In this case the reagent is no longer being excluded from those cells and now has accessibility for complex formation and therefore provides a negative stain for viability and a positive stain for compromised cells.

It is understood that cell samples may also be processed using fixation methods to allow for the analysis of cellular features as part of a wide range of techniques used in the life sciences. The fixation method and cell permeabilisation methods may vary but frequently results in membrane changes that allow the entry of live cell impermeant dyes.

Dye entry is preferably indicated by the acquisition of a fluorescence signal associated with the high affinity binding of the dye to intracellular nucleic acids and is invariably considered to be aided by fluorescence enhancement upon binding.

Cell-impermeant (and cell-permeant) fluorescent dyes, which variably bind to nucleic acids, are a large group of molecular probes used extensively in the biosciences and readily available from commercial suppliers. Sought features of these agents include: nucleic acid selectivity, excitation and emission characteristics, quantum yield, the potential for fluorescence enhancement upon binding, performance in aqueous environments, degree of exclusion from non-compromised cells (providing a negative stain for viability and a positive stain for cell death) or rapidity of penetration into intact cells for intact cell assays. Selection of a particular dye is often determined by the degree of spectral overlap with other fluorophores incorporated into an assay and the availability of convenient light sources for selective or optimal excitation.

Since the process of cell death frequently involves the sequential acquisition of changes in cellular properties over extended time-frame (minutes to days) there is a need for cell impermeant dyes that have negligible toxicity so that the continual presence of a given dye does not influence the reporting of the loss of viability within an assay. Such a non-toxic cell impermeant dye is preferred for the continuous monitoring of loss of viability in long term assays.

It is recognised that the extent of the fluorescence staining properties of cell chromatin, in cells with varying levels of structural integrity, by permeant and non-permeant dyes is complex and not readily predicted (Wlodkowic, Skommer et al. 2007). Cells undergoing cell death processes, permitting cellular entry of otherwise cell impermeant indicator dyes, also undergo changes in cellular structures not least in chromatin conformation. Hyperchromatic staining of apoptotic nuclei with absorption cationic dyes is frequently observed while apoptotic cell nuclei often appear dim with many DNA fluorochromes. Current understanding is that the enhanced affinity of the chromatin of early apoptotic cells for cationic dyes is associated with conformational relaxation rather than degradation of DNA (Erenpreisa, Freivalds et al. 1997). In late apoptotic cells, the very dense packaging of degraded DNA promotes further aggregation of dyes (Erenpreisa, Freivalds et al. 1997) affecting fluorescence properties (Erenpreisa, Freivalds et al. 1997).

Fluorescent staining of cells with nucleic acid targeting dyes is therefore a complex matrix of cell status, permeation properties, dye binding specificity, dye binding modes and dye-dye interactions. To offset such problems in cell based assays, the traditional approach has been to prefer high fluorescence enhancement and high quantum yield dyes. A wide range of cell impermeant dyes have found applications in nucleic acid staining. The most frequently used example is propidium iodide (PI).

The intensely fluorescent PI signal has the advantage of simple and sensitive detection, but there are disadvantages when this fluorochrome is incorporated into multi-colour analyses. Furthermore, PI has the capacity to be excited at UVA (eg 365 nm) wavelengths and by blue light (eg 488 nm) wavelengths, complicating its application when differential excitation is being used to distinguish a fluorescent analyte or an analyte detected by a fluorescent, probe. PI has no colorimetric signature for convenient analysis of cell staining. In particular, compensation must be applied to the signals gathered in parts of the visible spectrum adjacent to the peak emission region being analysed for PI to account for 'spill over'. Additionally, fluorescence emissions of PI may occupy a region of the spectrum in which emissions originating from a fluorescent analyte, or an analyte detected by a fluorescent probe, may need to be distinguished. PI offers some spectral advantage as a five cell impermeant dyes that emit in the red region and beyond (eg >620 nm wavelength).

It is understood that the high fluorescence intensity of PI hound to DNA frequently requires analysis of acquired fluorescence signals from cell populations on a logarithmic scale providing a wide dynamic range for the identification cell subpopulations.

U.S. Pat. No. 5,057,413 teaches the use of the cell permeant nucleic acid dye LDS-751 where preference for DNA distinguishes between damaged and intact cells based on the amount of fluorescence emitted. In another example, a distinction between intact and dead cells is enabled using the dye 7-AAD (with low intact cell permeation properties) in the flow cytometric leukemia/lymphoma assessment of the expression of the leukocyte marker (CD45) to avoid the pitfalls of non-specific staining (Shenkin, Babu et al. 2007). In yet another example, United States Patent Application 20070082377 discloses the use of the cell impermeant DNA dye 7-AAD as a component in multiparametric assays which also utilise a fluorescent probe that is a membrane stain, and a fluorescent probe that is a cell-permeable apoptosis-detection probe that binds to active caspase enzymes. Such approaches permit the distinction between dead or necrotic cells (detected using the vital stain 7-AAD; when this stain binds to or intercalates with DNA, it becomes detectable, e.g., through a process of fluorescence enhancement upon binding to a nucleic acid) and apoptotic cells characterized by modified caspase activity.

'Dual dye' assays utilising cell permeant and cell impermeant dyes are known (Giao, Wilks et al, 2009; Biggerstaff, Le Puil et al, 2006; Lehtinen, Nuutila et al 2004; Wlodkowic and Skommer, 2007a; Wlodkowic and Skommer, 2007b). The dyes used are invariably optimised for individual performance and effectively seek to avoid interactions so that cells can report permeation characteristics accurately. The dual dye arrays discussed above have individually various disadvantages and unfavourable properties which are associated with the precise systems employed. However, there is also a fundamental problem in dual dye assays that, without exception, direct binding cell-permeant nucleic acid stains will also stain nucleic acids in cells with compromised or disrupted membranes.

The dynamic range of signals obtained from cell permeant and cell impermeant dyes as described above provide for convenient methods of analysis.

Additionally, there is an ongoing need to improve the useful properties of fluorescent dyes for analysis of cells and other biological material.

The present invention, in at least some of its embodiments, addresses the above-described problems and needs. In particular, the present invention, in at least some of its embodiments, provides improved cell impermeant dyes, and also provides an improved system which can be used for live/dead cell discrimination using cell impermeant and cell permeant dyes, in some embodiments, the invention provides cell impermeant dyes having a preferred emission in the far red (eg >660 nm wavelength or >690 nm wavelength) and with reduced emission in the orange/red spectral region (eg >530<620 nm wavelengths).

According to a first aspect of the invention there is provided a compound of Formula (I):

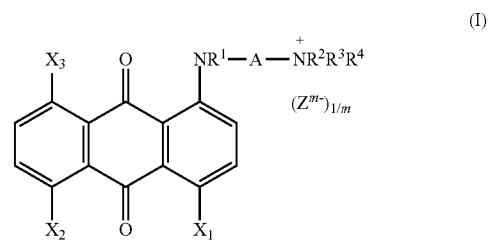

In which: A is a $C_{2-8}$ alkylene group; $R^1$, $R^2$, $R^3$, and $R^4$ are independently selected from hydrogen, $C_{1-4}$ alkyl, $C_{2-4}$ dihydroxyalkyl in which the carbon atom attached to the nitrogen atom does not carry a hydroxyl group and no carbon atom is substituted by two hydroxyl groups, or $R^2$ and $R^3$ together form a $C_{2-6}$ alkylene group which with the nitrogen atom to which $R^2$ and $R^3$ are attached forms a heterocyclic ring;

$X_1$, $X_2$ and $X_3$ are independently selected from hydrogen, hydroxyl, $NR^1\text{-}A\text{-}NR^2R^3R^{4+}(Z^{m-})_{1/m}$ halogeno amino, $C_{1-4}$ alkoxy or $C_{2-8}$ alkanoyloxy; and $(Z^{m-})_{1/m}$ is an anion of charge m;

or a derivative in which the group $NR^1$ is quaternarised.

Preferably m is 1.

Numerous advantages are associated with at least some of these compounds when used as dyes for analysing cells and other biological material. The advantages include:

Wafer solubility for ready incorporation into assays at a range of concentrations compatible with the isotonic buffer conditions commonly used in cell-based assays.

Chemical purity and stability for reproducible deployment within multiple assays and convenient storage.

Red/far-red fluorescence properties for ready incorporation info multiparameter assays with visible range floors with little or no spectral overlap, or orange fluorescence for easy use with red floors High affinity nucleic acid binding properties for applications requiring the analysis of nucleated cells.

Non-enhancement of fluorescence upon binding to a nucleic acid to enable a known degree of stoichiometry between the intensity of fluorescence emission and the degree of DNA binding.

Low intrinsic fluorescence to provide for a relative reduction in background fluorescence of unbound dye versus the increased signal upon nuclear binding attributable to the localised concentration of bound molecules.

Cell impermeant properties for the selective and positive staining of cells with compromised membrane or having an inability to exclude dye molecules.

Nuclear discriminating properties in fixed cells for use as a direct DNA stain for all nucleated cells with detection of fluorescence emission by imaging or flow cytometry or other detection platforms.

Low toxicity towards intact cells so that the dye can be co-incubated with cells for extended periods during a biological application without deleterious effects such as the inhibition of proliferation.

A combination of the above properties that allows for the time-dependent analysis of the loss of cellular integrity monitored by the incubation of cells with a cell impermeant dye over variable periods and the episodic sampling of the same population for the detection of cell staining.

The present invention provides quaternarised aminoalkylamino anthraquinone compounds which may be used as inter alia fluorescent dyes. A quaternarised aminoalkylamino substituent is present at least the 1 position. Further quaternarised aminoalkylamino substituents may be present at the 4, 5, or 8 positions, or combinations thereof. International publications WO91/05824 and WO99/65992 (the entire contents of both of which are herein incorporated with reference) disclose various kinds of aminoalkylamino anthraquinone compounds which can toe used as precursors to the synthesis of compounds of the present invention.

Preferably, at least one of $X_1$, $X_2$ and $X_3$ are independently $NR^1\text{-}A\text{-}NR^2R^3R^4+(Z^{m-})_{1/m}$. In particularly preferred embodiments, $X_2$ (but not $X_1$ and $X_3$) is $NR^1\text{-}A\text{-}NR^2R^3R^4+ (Z^{m-})_{1/m}$, ie, an anthraquinone substituted at the 1,5 positions with quaternarised aminoalkylamino groups.

In another preferred class of compounds, $X_1$ (but not $X_2$ and $X_3$) is $NR^1\text{-}A\text{-}NR^2R^3R^4+(Z^{m-})_{1/m}$ie, anthraquinones having quaternarised aminoalkylamino substituents at the 1,4 positions. 1,8 substituted analogues are also possible.

Advantageously, $X_1$ and $X_3$ are both hydroxyl.

In the other preferred embodiments, $X_1$ and $X_3$ are both hydrogen.

Preferably, $R^1$ is hydrogen, although it is possible to utilise compounds in which the amino moiety at this position is a tertiary amine. In these embodiments, it is preferred that $R^1$ is a $C_{1-4}$ alkyl.

It is preferred that $R^2$, $R^3$ and $R^4$ are $C_{1-4}$ alkyl. Advantageously, $R^2$, $R^3$ and $R^4$ are methyl.

In preferred embodiments, A is $(CH_2)_2$.

In a particularly preferred embodiment, the compound is of formula (IA):

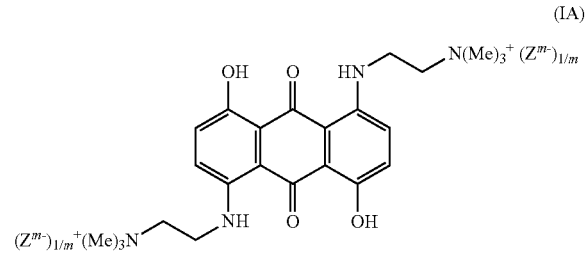

(IA)

Another preferred compound is a formula (IB):

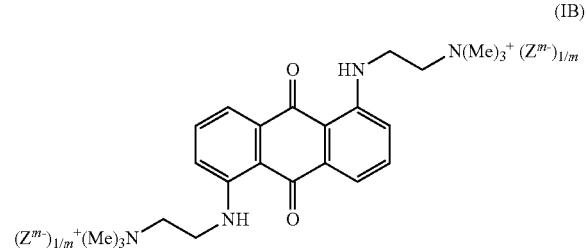

(IB)

Specific examples of compounds of the invention are provided by the compounds listed below in combination with a suitable counter-anion, such as iodide.

1-{[2-(trimethylamino)ethyl]amino}anthracene-9,10-dione

1-{[2-(trimethylamino)ethyl]amino}-5,8-dihydroxyanthracene-9,10-dione 1,8-Bis{[2-(trimethylamino)ethyl]amino}anthracene-9,10-dione 1,8-Bis{[2-(trimethylamino)ethyl]amino}-5,8-dihydroxyanthracene-9,10-dione 1,4-Bis{[2-(trimethylamino)ethyl]amino}anthracene-9,10-dione 1,4-Bis{[2-(trimethylamino)ethyl]amino}-5,8-dihydroxyanthracene-9,10-dione 1-{[2-(triethylamino)ethyl]amino}anthracene-9,10-dione 1-{[2-(triethylamino)ethyl]amino}5,8dihydroxyanthracene-9,10-dione 1,5-Bis{[2-(triethylamino)ethyl]amino}anthracene-9,10-dione 1,5-Bis{[2-(triethylamino)ethyl]amino}5,8dihydroxyanthracene-9,10-dione 1,4-Bis{[2-(triethylamino)ethyl]amino}anthracene-9,10-dione 1,4-Bis{[2-(triethylamino)ethyl]amino}5,8dihydroxyanthracene-9,10-dione 1,8-Bis{[2-(triethylamino)ethyl]amino}anthracene-9,10-dione 1,8-Bis{[2-(triethylamino)ethyl]amino}5,8dihydroxyanthracene-9,10-dione 1-{[2-(trimethylamino)propyl]amino}-5,8dihydroxyanthracene-9,10-dione iodide 1,8-Bis{[2-(trimethylamino)propyl]amino}-5,8dihydroxyanthracene-9,10-dione 1,5-Bis{[2-(trimethylamino)propyl]amino}-5,8dihydroxyanthracene-9,10-dione 1,4-Bis{[2-(trimethylamino)propyl]amino}-5,8dihydroxyanthracene-9,10-dione 1-{[2-(triethylamino)propyl]amino}-5,8dihydroxyanthracene-9,10-dione
1,5-Bis{[2-(triethylamino)propyl]amino}-5,8dihydroxyanthracene-9,10-dione
1,4-Bis{[2-(triethylamino)propyl]amino}-5,8dihydroxyanthracene-9,10-dione
1,8-Bis{[2-(triethylamino)propyl]amino}-5,8dihydroxyanthracene-9,10-dione
1,5-Bis{[2-(triethylamino)butyl]amino}anthracene-9,10-dione
1,4-Bis{[2-(triethylamino)butyl]amino}anthracene-9,10-dione
1,8-Bis{[2-(triethylamino)butyl]amino}anthracene-9,10-dione
1,5-Bis{[2-(triethylamino)butyl]amino}-5,8dihydroxyanthracene-9,10-dione
1,4-Bis{[2-(triethylamino)butyl]amino}-5,8dihydroxyanthracene-9,10-dione
1,8-Bis{[2-(triethylamino)butyl]amino}-5,8dihydroxyanthracene-9,10-dione The compounds of the present invention may include any suitable counter-anions. Examples of counter-anions are halides such as chloride, bromide and iodide, physiologically acceptable anions derived from inorganic acids such as phosphoric and sulphuric acids, and organic acids such as acetic, ascorbic, benzoic, citric, fumaric, gluconic, isethionic, lactic, maleic, malic, methane sulphonic, oxalic, succinic, sulphamic and tartaric.

The compounds of the present invention can be conveniently prepared by quaternarisation of an aminoalkylamino precursor compound to the compound of formula (I). The quaternarisation process can comprise alkylation of the precursor (for example using an alkyl halide reagent) or quaternarisation through formation of an acid addition salt using a suitable organic or inorganic acid. The aminoalkylamino anthraquinone compounds discussed previously in connection with International publications WO91/05824 and WO99/85092 can serve as suitable precursor compounds to the quaternarisation step. Other routes for the synthesis of the precursor compounds which are quaternarised to produce the compounds of the present invention would be readily apparent to the skilled reader.

The invention extends to a composition including a compound of formula (I) as defined above with a physiologically acceptable diluent or carrier.

According to a second aspect of the invention there is provided a fluorescent complex including a nucleic acid and a compound of Formula (I):

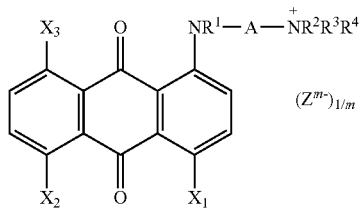

in which: A is a $C_{2-8}$ alkylene group; $R^1$, $R^2$, $R^3$, and $R^4$ are independently selected from hydrogen, $C_{1-4}$ alkyl, $C_{2-4}$ dihydroxyalkyl in which the carbon atom attached to the nitrogen atom does not carry a hydroxyl group and no carbon atom is substituted by two hydroxyl groups, or $R^2$ and $R^3$ together form a $C_{2-5}$ alkylene group which with the nitrogen atom to which $R^2$ and $R^3$ are attached forms a heterocyclic ring;

$X_1$, $X_2$ and $X_3$ are independently selected from hydrogen, hydroxyl, $NR^1$-A-$NR^2R^3R^4$+$(Z^{m-})_{1/m}$, halogeno amino, $C_{1-4}$ alkoxy or $C_{2-8}$ alkanoyloxy; and $(Z^{m-})_{1/m}$ is an anion of charge m;

or a derivative in which the group $NR^1$ is quaternarised.

The nucleic acid may be DNA, and the DNA may be present in a cell. The DNA may be present in a non-intact cell.

According to a third aspect of the invention there is provided a method of analysing a sample of cells or other biological material containing nucleic acid including the steps of.
a) preparing a biologically compatible solution containing a compound of Formula (I);

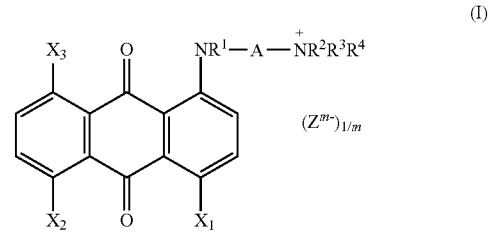

in which: A is a $C_{2-8}$ alkylene group; $R^1$, $R^2$, $R^3$, and $R^4$ are independently selected from hydrogen, $C_{1-4}$ alkyl, dihydroxyalkyl in which the carbon atom attached to the nitrogen atom does not carry a hydroxyl group and no carbon atom is substituted by two hydroxyl groups, or $R^2$ and $R^3$ together form a $C_{2-6}$ alkylene group which with the nitrogen atom to which $R^2$ and $R^3$ are attached forms a heterocyclic ring:

$X_1$, $X_2$ and $X_3$ are independently selected from hydrogen, hydroxyl, $NR^1$-A-$NR^2R^3R^4$+$(Z^{m-})_{1/m}$, halogeno amino, $C_{1-4}$ alkoxy or $C_{2-8}$ alkanoyloxy; and $(Z^{m-})_{1/m}$ is an anion of charge m;

or a derivative in which the group $NR^1$ is quaternarised;
b) treating a sample of cells or other biological material with the biologically compatible solution; and
c) detecting a spectroscopic property associated with the absorption of electromagnetic radiation by the compound of Formula (I).

Advantageously, the spectroscopic property associated with absorption of electromagnetic radiation by the compound of Formula (I) is fluorescence, and step c) includes exciting the compound of Formula (I) with electromagnetic radiation, and detecting an emitted fluorescence signal. Fluorescence intensity in pre-defined spectral regions may be measured, although other detection schemes, such as measurements of fluorescence lifetimes, may be used.

Alternatively, the spectroscopic property associated with the absorption of electromagnetic radiation by the compound of Formula (I) may be a colorimetric property.

Advantageously, the method may be used for discrimination of cellular nuclei in the sample of cells, in which step b) is performed to cause binding of nucleic acid in cellular nuclei by the compound of Formula (I), and the discrimination of the cellular nuclei is based at least in part on the spectroscopic property detected in step c).

Step b) may be performed to stain the sample of cells with the compound of Formula (I). Advantageously, the method may be one in which cell death accruement is monitored, wherein step b) is performed prior to or during an assay period thereby enabling a continuous or frequent readout of cell death accruement during the assay period. Compounds of Formula (IA) are particularly preferred for use in these methods. This approach takes advantage of the non-toxicity of impermeant compounds of the present invention. This means that it is possible to include a compound of Formula (I) with a cell mixture so that the compound of Formula (I) is present during the test. As a cell dies (eg from the influence of a test compound in an assay) the cell becomes stained with the compound of Formula (I). The compound of Formula (I) may be added before, during or after any treatment that might cause call death. This permits sampling during a test which may be made on a continuous basis.

Step c) may include detecting fluorescence emitted by individual cells by flow cytometry, infra-cellular location detection by fluorescence microscopy, or any other suitable kind of fluorescence based detection technique. Imaging techniques may be employed. It is understood that a range of imaging systems may be employed for the analysis of fluorescence signals, including but not exclusively fluorescence intensity, polarisation, fluorescence life time, fluorescence spectrum, and spatial disposition of such qualities within a specimen or sample being analysed.

In certain preferred embodiments, fixed or permeabilised cells are analysed, wherein the sample of cells are fixed by treatment with a fixative or permeabilising agent. The discrimination and staining of cellular nuclei in fixed and permeabilised cells are particularly preferred embodiments.

In other preferred embodiments, step b) further includes treating the sample with at least one other fluorochrome or light-emitting compound, and step c) further includes detecting a spectroscopic property associated with the absorption of electromagnetic radiation by the fluorochrome or light-emitting compound.

The steps b) and c) associated with the other fluorochrome or light-emitting compound may be performed simultaneously with, or separately from, the steps b) and c) associated with the compound of Formula (I).

In a particularly preferred embodiment, the method discriminates between intact and non-intact cells, in which the compound of formula (I) is cell impermeant, step b) further includes treating the sample with a second fluorochrome or light-emitting compound which is cell permeant, and step c) further includes detecting a spectroscopic property associated with the absorption of electromagnetic radiation by the second fluorochrome or light-emitting compound, wherein the detection of the spectroscopic property associated with the absorption of electromagnetic radiation by the compound of Formula (I) is correlated with the presence of non-Intact cells, and the detection of the spectroscopic property associated with the absorption of electromagnetic radiation by the second fluorochrome or light-emitting compound is correlated with the presence of intact cells.

Non-intact cells are understood to include dead cells, and damaged cells with compromised or disrupted membranes.

Advantageously, the second fluorochrome or light-emitting compound has a binding potential (which is preferably, but not necessarily, related to binding affinity) for nucleic acid and/or other macromolecular material in the discriminated cells which is lower than that of the compound of Formula (I), and as a consequence competes less efficiently in the presence of the compound of Formula (I) for binding to the nucleic acid and/or other macromolecular material in the discriminated cells so that the second fluorochrome or light-emitting compound is substantially excluded from binding to non-intact cells or masked by the compound of Formula (I).

The preferred full exclusion of the second fluorochrome or light-emitting compound by the compound of Formula (I) in damaged cells provides for optimal discrimination on the basis of the dual analysis of fluorescence emissions. Further the fluorescence signal from the second fluorochrome or light-emitting compound is effectively eliminated in damaged cells optimally labelled with compound of Formula (I) but could also be detectable at an attenuated level by simply changing the ratio of compound of Formula (I) to that of the second fluorochrome or tight-emitting compound providing for a ratio-metric analysis of fluorescence attained by the range of co-staining conditions as described above. Preferably the molar ratios of compounds of the compound of Formula (I) to that of the second fluorochrome or light-emitting compound would be within the range of 1:10 and 10:1 and more preferably 3:20. Preferably, the staining of intact cells exclusively reporting the presence of the second fluorochrome or light-emitting compound provides additional information of value in determining cell status including, but not exclusively: cell biomass related to total dye binding and the presence of intracellular nucleic acid as a positive fluorescence discriminator for nucleated cells. Preferable indications of changes in cellular biomass permit distinction to be made between cells continuing to progress metabolically without intervening cell division preferably in the analysis of cell undergoing long term inhibition of proliferation or cell cycle arrest.

Preferably, the second fluorochrome or light-emitting compound is a compound of Formula (II):

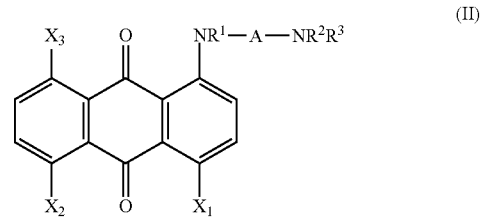

(II)

or an N-oxide derivative thereof;

in which: A is a $C_{2-6}$ alkylene group; $R^1$, $R^2$, and $R^3$ are independently selected from hydrogen, $C_{1-4}$ alkyl, $C_{2-4}$ dihydroxyalkyl in which the carbon atom attached to the nitrogen atom does not carry a hydroxyl group and no carbon atom is substituted by two hydroxyl groups, or $R^2$ and $R^3$ together form a $C_{2-6}$ alkylene group which with the nitrogen atom to which $R^2$ and $R^3$ are attached forms a heterocyclic ring; and $X_1$, $X_2$ and $X_3$ are independently selected from hydrogen, hydroxyl, $NR^1$-A-$NR^2R^3$, halogeno amino, $C_{1-4}$ alkyloxy or $C_{2-8}$ alkanoyloxy.

In preferred embodiments the compound of Formula (II) is a 1,5 amino substituted anthraquinone, ie, $X_2$ is $NR^1$-A-$NR^2R^3$ but $X_1$ and $X_3$ are not.

A particularly preferred embodiment of this class of 1,5 amino substituted anthraquinones is a compound of Formula (IIA)

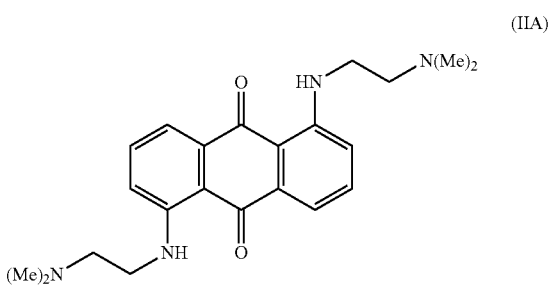

Advantageously, discrimination between intact and non-intact cells is made after the sample of cells is exposed to an agent which is potentially cytotoxic or otherwise capable of inducing cell death, in order to monitor the effect of the agent on the sample of cells.

In further preferred embodiments, step b) further includes treating the sample with at least a third fluorochrome or light-emitting compound, and step c) further includes detecting a spectroscopic property associated with the absorption of electromagnetic radiation by at least the third fluorochrome or light-emitting compound and correlating said spectroscopic property with a feature or property of intact cells and/or non-intact cells.

The detected spectroscopic property of the third fluorochrome or light-emitting compound may be similar to the detected spectroscopic property of the compound of Formula (I), and distinct from the detected spectroscopic property of the second fluorochrome or light-emitted compound, wherein the detected spectroscopic property of the third fluorochrome or light-emitting compound is correlated with a feature or property of intact cells.

The defected spectroscopic property of the third fluorochrome or light-emitting compound may be similar to the detected spectroscopic property of the second fluorochrome or light-emitting compound and distinct from the detected spectroscopic property of the compound of Formula (I), wherein the detected spectroscopic property of the third fluorochrome or light-emitting compound is correlated with a feature or property of non-intact cells.

Preferably, the defected spectroscopic properties in step c) are emitted fluorescence in a pre-defined region of the electromagnetic spectrum, and step c) includes exciting the compound of Formula (I), the second and, optionally, the third and any further, fluorochrome or light-emitting compound with electromagnetic radiation.

Advantageously, the compound of Formula (I), the second and, optionally, the third fluorochrome or light-emitting compounds are co-excited by a single source of electromagnetic radiation.

Advantageously, emitted fluorescence of the third fluorochrome or light-emitting compound is in a pre-defined region of the electromagnetic spectrum which is i) similar to that of the emitted fluorescence of the compound of Formula (I), preferably in the red and/or near IR region, and ii) distinct from that of the emitted fluorescence of the second fluorochrome or light-emitting compound. The third fluorochrome may be Qdot 705 nm emitting nanocrystals.

Advantageously, emitted fluorescence of the third fluorochrome or light-emitting compound is in a predefined region of the electromagnetic spectrum which is i) similar to that of the emitted fluorescence of the second fluorochrome or light-emitting compound, preferably in the orange region, and ii) distinct from that of the emitted fluorescence of the compound of Formula (I).

In embodiments in which the method discriminates between intact and non-intact cells, step c) may be performed using flow cytometry, and or using fluorescence microscopy to provide information on cellular location of fluorescence emissions. It is understood that a range of imaging systems may be employed for the analysis of fluorescence signals, including but not exclusively fluorescence intensity, polarisation, fluorescence life time, fluorescence spectrum, and spatial disposition of such qualities within a specimen or sample being analysed.

Step c) may further include measurements of light scattering from cells. However, useful results can be obtained without requiring light scattering measurements to be performed as well.

Measurements may be made over a period of time in order to acquire time resolved date, for example to examine accrued changes in cellular integrity or to examine changes in discriminated intact cells as determined by characteristics correlated with the presence of the second and/or third fluorochromes or light-emitting compounds.

According to a fourth aspect of the invention there is provided a method of discriminating between intact and non-intact cells including the steps of:
a) preparing a biologically compatible solution containing a cell impermeant fluorochrome or light-emitting compound;
b) preparing a biologically compatible solution containing a cell permeant fluorochrome or light-emitting compound which has a binding potential (which is preferably, but not necessarily, related to binding affinity) for nucleic acid and/or other macromolecular material in the discriminated cells which is lower than that of the cell impermeant fluorochrome or light-emitting compound, and as a consequence competes less efficiently in the presence of the cell impermeant fluorochrome or light-emitting compound for binding to the nucleic acid and/or other macromolecular material in the discriminated cells so that the cell permeant fluorochrome or light-emitting compound is substantially excluded from binding to non-intact cells or masked by the cell impermeant fluorochrome or light-emitting compound;
c) treating a sample of cells with the biologically compatible solution or solutions; and
d) detecting a spectroscopic property associated with the absorption of electromagnetic radiation by the cell impermeant fluorochrome or light-emitting compound and correlating same with the presence of non-intact cells, and detecting a spectroscopic property associated with the absorption of electromagnetic radiation by the cell permeant fluorochrome or light-emitting compound and correlating same with the presence of intact cells.

In addition to the cell permeant dyes discussed above, the following dyes may be used as the cell permeant fluorochrome or light-emitting compound ('number/number' indicates wavelengths in nm for max Excitation versus max Emission):

Cell-permeant cyanine dyes (the SYTO nucleic acid stains) with lower affinity than the SYTOX dyes and capable of entering live cells preferably but not exclusively SYTO® 40 blue fluorescent nucleic acid stain SYTO® 58 red fluorescent nucleic acid stain, SYTO® 60 red fluorescent nucleic acid stain, SYTO® 81 red fluorescent nucleic acid stain, SYTO® 82 red fluorescent nucleic add stain, SYTO® 63 red fluorescent nucleic acid stain, SYTO® 64 red fluorescent nucleic acid stain, SYTOX® Blue nucleic acid stain, SYTO® 40 blue fluorescent nucleic acid stain, SYTO® 41 blue fluorescent nucleic acid stain, SYTO® 42 blue fluorescent nucleic acid stain, SYTO® 45 blue fluorescent nucleic acid stain, SYTO® 80 orange fluorescent nucleic acid stain, SYTO® 81 orange fluorescent nucleic acid stain, SYTO® 82 orange fluorescent nucleic acid stain, SYTO® 83 orange fluorescent nucleic acid stain, SYTO® 84 orange fluorescent nucleic acid stain, SYTO® 85 orange fluorescent nucleic acid stain, SYTOX® Orange nucleic acid stain, SYTO® 10 green fluorescent nucleic acid stain, SYTO® 9 green fluorescent nucleic acid stain, SYTO® BC green fluorescent nucleic acid stain, SYTOX® Blue dead cell stain, SYTOX® Green nucleic acid stain, SYTO® 21 green fluorescent nucleic acid stain, SYTO® 24 green fluorescent nucleic acid stain, SYTO® 25 green fluorescent nucleic acid stain, SYTO® 11 green fluorescent nucleic acid stain, SYTO® 12 green fluorescent nucleic acid stain, SYTO® 13 green fluorescent nucleic acid stain, SYTO® 14 green fluorescent nucleic acid stain, SYTO® 18 green fluorescent nucleic acid stain, and SYTO® 17 red fluorescent nucleic acid stain.

DAPI: UV-excitable DNA binding fluorochrome 4',6-diamidino-2-phenylindole, dihydrochloride (DAPI) (Ex358/Em46) or 4',6-diamidino-2-phenylindole, dilactate (DAPI, dilactate)

Minor groove binding Hoechst dyes preferably but not exclusively Hoechst 34580, Hoechst 33258 (bis-benzimide) as the pentahydrate being a blue fluorescent (Ex352/Em461) AT-selective, minor groove-binding dsDNA-selective fluorochrome, Hoechst 33342: as the trihydrochloride, trihydrate, being a blue fluorescent (Ex350/Em461) AT-selective, minor groove-binding dsDNA-selective binding LDS 751 being a nucleic acid stain: (Ex543/Em712) (DNA) (Ex590/Em607) (RNA)

7-Aminoactinomycin D (7-AAD; Ex546/Em647)

Acridine orange showing metachromatic staining of cells with red biased emission with RNA and green biased emission for DNA In addition to the cell impermeant dyes discussed above, the following dyes may be used as the cell impermeant fluorochrome or light-emitting compound ('number/number' indicates wavelengths in nm for max Excitation versus max Emission):

cyanine dimers of the TOTO family cyanine dimer dyes, preferably but not exclusively TOTO®-1 iodide (514/533), TO-PRO®-1 iodide (515/531), TOTO®-3 iodide (642/660)

cyanine monomers of the TO-PRO family of dyes, preferably but not exclusively YO-PRO-1 (Ex491/Em509), TO-PRO-1 (Ex515/Em531), TO-PRO-®-Iodide (642/661), TO-PRO®-5 iodide (745/770), YOYO®-1 iodide (491/509), YO-PRO®-1 iodide (491/509), YOYO®-3 iodide (612/631), YO-PRO®-3 iodide (612/631).

nucleic acid SYTOX dyes preferably hut not exclusively SYTOX Blue (Ex445/Em470), SYTOX Green (Ex504/Em523) and SYTOX Orange (Ex547/Em570).

propidium iodide (PI; Ex530/Em625) and cell-impermeant ethidium bromide (EthBr; Ex518/Em605)

7-Aminoactinomycin D (7-AAD; Ex546/Em647)

Acridine orange metachromatic staining of cells with red biased emission with RNA and green biased emission for DNA.

If is understood that a range of detection systems may foe employed for the analysis of the different fluorescence signals obtained using the invention, including but not exclusively fluorescence intensity, polarisation, fluorescence life time, fluorescence spectrum. It is further understood that cellular imaging methods may additionally provide spatial disposition and dynamic analyses of such qualities within a specimen or of a sample being analysed.

According to a fifth aspect of the invention there is provided a detection system for use in a method according to the third or fourth aspects of the invention, the system including:

one or more sources of electromagnetic radiation for exciting fluorochromes and light-emitting compounds used in the method;

a plurality of detectors for detecting spectroscopic properties associated with the absorption of electromagnetic radiation by the fluorochromes and light-emitting compounds; and a detector analysis system adapted to correlate the detected spectroscopic properties with the presence of intact and non-intact cells thereby to discriminate between intact and non-intact cells.

Preferably, the detectors are fluorescence detectors.

Highly advantageously, the detection system may have a single source of electromagnetic radiation for co-exciting the fluorochromes and light-emitting compounds.

Highly advantageously, the plurality of detectors are in the form of a pair of detectors which defect the spectroscopic properties of all of the fluorochromes and light-emitting compounds.

The invention may be applied to the investigation of cell integrity in a diverse range of cell types and applications. Where mention is made herein of a cell or cell type, it is preferred that the cell or cell type is a live eukaryotic cell. The invention can be used in conjunction with ail cell types. The cells may be selected without limitation from the following cell types:

Animal cells including human and mammalian cells derived as biopsy specimens (e.g., by fine needle aspirates), as tissue explants, as primary cultures (e.g., human skin fibroblasts), as transformed cell lines (e.g., SV40 transformed fibroblasts), as immortalized cell lines (e.g., cell lines immortalized with human telomerase reverse transcriptase [hTERT]), or as established tumour cell lines.

Plant cells and bacterial cells.

Human tumour cell lines including those representing specific sites and diseases of therapeutic, diagnostic and analytical interest, preferably those capable of demonstrating adherent growth on a substrate, for example: Brain Cancer, Bladder Cancer, Breast Cancer, Colon and Rectal Cancer, Endometrial Cancer, Kidney Cancer (Renal Cell), Leukaemia, Lung Cancer, Melanoma, Pancreatic Cancer, Prostate Cancer, Skin Cancer (Non-melanoma), Thyroid Cancer. Also, Human tumour cell lines routinely available for the purpose of drug screening methodologies such as those indicated in the US National Cancer Institute tumour cell line panel NCI-60 (ref: dtp.nci.nih.gov/docs/misc/common_files/cell_list.html):

| Cell Line | NCI-60 Panel Name |
| --- | --- |
| A549/ATCC | Non-Small Cell Lung |
| EKVX | Non-Small Cell Lung |
| HOP-62 | Non-Small Cell Lung |
| HOP-92 | Non-Small Cell Lung |
| NCI-H226 | Non-Small Cell Lung |
| NCI-H23 | Non-Small Cell Lung |
| NCI-H322M | Non-Small Cell Lung |
| NCI-H460 | Non-Small Cell Lung |

| Cell Line | NCI-60 Panel Name |
| --- | --- |
| NCI-H522 | Non-Small Cell Lung |
| COLO 205 | Colon |
| HCC-2998 | Colon |
| HCT-116 | Colon |
| HCT-15 | Colon |
| HT29 | Colon |
| KM12 | Colon |
| SW-620 | Colon |
| SF-268 | CNS |
| SF-295 | CNS |
| SF-539 | CNS |
| SNB-19 | CNS |
| SNB-75 | CNS |
| 0251 | CNS |
| LOX IMVI | Melanoma |
| MALME-3M | Melanoma |
| M14 | Melanoma |
| SK-MEL-2 | Melanoma |
| SK-MEL-28 | Melanoma |
| SK-MEL-5 | Melanoma |
| UACC-257 | Melanoma |
| UACC-62 | Melanoma |
| IGR-OV1 | Ovarian |
| OVCAR-3 | Ovarian |
| OVCAR-4 | Ovarian |
| OVCAR-5 | Ovarian |
| OVCAR-8 | Ovarian |
| SK-OV-3 | Ovarian |
| 786-0 | Renal |
| A498 | Renal |
| ACHN | Renal |
| CAKI-1 | Renal |
| RXF 393 | Renal |
| SN12C | Renal |
| TK-10 | Renal |
| UO-31 | Renal |
| PC-3 | Prostate |
| DU-145 | Prostate |
| MCF7 | Breast |
| MDA-MB-231/ATCC | Breast |
| HS 578T | Breast |
| MDA-MB-435 | Breast |
| BT-549 | Breast |
| T-47D | Breast |
| LXFL 529 | Non-Small Cell Lung |
| DMS 114 | Small Cell Lung |
| DLD-1 | Colon |
| KM20L2 | Colon |
| SNB-78 | CNS |
| XF 498 | CNS |
| RPMI-7951 | Melanoma |
| M19-MEL | Melanoma |
| RXF-631 | Renal |
| SN12K1 | Renal |
| MDA-MB-468 | Breast |

Human tumour cell lines selected for their functional expression of specific molecular entities such as transporters of xenobiotic molecules (e.g., the ABCA3 drug transporter expressing in lung cancer lines H522M, A549, and EKVX) and human tumour cells selected for their convenient performance in gene transfer studies (e.g., U2-OS human osteosarcoma cells).

Mammalian cell lines used in functional genomics studies (e.g., NIH 3T3 murine cell line)

Single-cell forms of vertebrates (e.g., components of embryos, larval forms or cells derived from dissociated cell preparations of zebrafish Danio [Brachydanio] redo).

Cell lines used in ADME/Tox (Absorption, Distribution, Metabolism, Elimination/Toxicity) screening protocols (e.g., hepatocyte derived cell lines such as HepG2).

Embryonic stem cells derived from human or murine sources.

Adult Stem Cells

Neurones and/or supporting cells of the central nervous system (e.g. astrocytes, oligodendrocytes, microglia and Schwann cells).

Immortal somatic cell hybrids including hybrids that secrete antibodies (e.g. hybridomas).

Stem Cell Versus Non-Stem Cells

Nucleated Cell Blood Components

Senescent, non-senescent, adherent, non-adherent, quiescent and non-quiescent cells.

Applications may be selected without limitation from the following areas of investigation:

Changes in cell integrity due to physiological changes in cells (e.g., differentiation or change in growth phase).

Changes in cell integrity due to changes in cells in response to a disease process.

Changes in cell integrity induced by infective agents including bacteria and viruses Changes in cell integrity induced by a parasite.

Changes in cell integrity due to changes in cells in response to a physical agent (e.g., ionising and non-ionising radiations).

Changes in cell integrity due to the incorporation of optical active physical agents (e.g., quantum-well carrying nanoparticles) or chromatic dyes.

Changes in cell integrity due to changes in cells in response to an known or unknown bioactive agent for the purpose of.

Changes in cell integrity as a monitor for environmental sensing of toxins (e.g., heavy metal contamination).

Changes in cell integrity of nanoparticle toxicity with the advantage that cells carrying a toxic load of particles can be co-located with fluorescent dyes for definitive analysis using electron microscopy or other high resolution imaging approaches.

Changes in cell integrity for the detection of toxins (e.g., endotoxin sensing for bio-safety).

Changes in cell integrity for the detection of toxic or harmful agents for security monitoring purposes and rapid diagnostics.

Changes in cell integrity for the monitoring the progress of a fermentation process (e.g., yeast life cycle in a brewing application).

Changes in cell integrity for the monitoring the progress of a biopharmaceutical preparation process (e.g., cytokine production).

Changes in cell integrity to discern state transitions associated with cell death (apoptosis or necrosis).

Changes in cell integrity for the analysis of cell cycle progression in physiological and pathological systems.

Analysis of pharmacodynamic responses for the purpose of drug screening or discovery.

Changes in cell integrity for the study of cellular systems that modulate cell structure and function as they undergo state changes under the influence of internal programmes or enforced by perturbing agents (e.g., cytoskeleton or chromatin modulating agents

REFERENCES CITED

Biggerstaff, J. P., M. Le Puil, et. al. (2006), "New methodology for viability testing in environmental samples." *Mol Cell Probes* 20(2): 141-6.

Darzynkiewicz, Z., G. Juan, at al. (1997). "Cytometry in cell necrobiology: analysis of apoptosis and accidental cell death (necrosis)." *Cytometry* 27(1): 1-20.

Erenpreisa, J., T. Freivalds, et al. (1997), "Apoptotic cell nuclei favour aggregation and fluorescence quenching of DNA dyes." *Histochem Cell Biol* 108(1): 67-75.

Giao, M. S., S. A. Wilks, et al. (2009). "Validation of SYTO 9/propidium iodide uptake for rapid detection of viable but noncultivable *Legionella pneumophila.*" *Microb Ecol* 58(1): 56-62.

Lehtinen, J., J. Nuutila, et al. (2004). "Green fluorescent protein-propidium iodide (GFP-PI) based assay for flow cytometric measurement of bacterial viability." *Cytometry A* 60(2): 165-72.

Shenkim M., R. Babu, et al. (2007), "Accurate assessment of cell count and viability with a flow cytometer," *Cytometry B Clin Cytom* 72(5): 427-32.

Wlodkowic, D. and J. Skommer (2007a), "SYTO probes: markers of apoptotic cell demise." *Curr Protoc Cytom* Chapter 7: Unit7 33.

Wlodkowic, D., J. Skommer, et al. (2007b). "Towards an understanding of apoptosis defection by SYTO dyes." *Cytometry A* 71(2): 61-72.

Whilst the invention has bean described above, it extends to any inventive combination of the features set out above, or in the following description, drawings or claims. For example, elements of one aspect of the invention may be incorporated with elements of another aspect of the invention.

Embodiments of compounds, fluorescent complexes, methods and detection systems in accordance with the invention will now be described with reference to the accompanying drawings, in which:—

FIG. 1 is a diagram of excitation and fluorescence spectra for (a) a number of dyes (b) Compound of Formula (IIA) (c) a compound of Formula (IA);

FIG. 2 is a diagram of fluorescence obtained using a combination of cell permeant and cell impermeant dyes of the invention in conjunction with (a) live cells and (b) dead cells;

FIG. 5 is a diagram of fluorescence obtained via a detection system using a compound of Formula (IA)/Compound (IIA) dye combination;

FIG. 6 is a diagram of fluorescence obtained from a two colour three fluorochrome detection system;

FIG. 8 shows absorbance and emission spectra for a compound of Formula (IA);

FIG. 9 shows fluorescence obtained from experiments using Annexin V-FITC in combination with (a) propidium iodide (PI) with PI fluorescence intensity on a log scale (b) a compound of Formula (IA), with compound of Formula (IA) fluorescence intensity shown on a linear scale (c) a compound of Formula (IA). with a compound of Formula (IA) fluorescence intensity shown on a log scale;

FIG. 10 shows prominent nuclear staining of fixed U-2 OS human osteosarcoma cells using a compound of Formula (IA);

FIG. 11 shows the staining of cells with compromised membranes using a compound of Formula (IA);

FIG. 12 shows the effect of incubation of human B cell lymphoma cells revealing low toxicity of a compound of Formula (IA);

FIG. 13 shows early stage cell death and corresponding loss in mitochondrial and plasma membrane integrity in human Jurkat cell death in response to staurospurine; and FIG. 14 shows combination tracking of cell state with co-targeted fluorescent probes compound (IA) (dead cells) and compound (IIA) (live cells).

Figure 3:
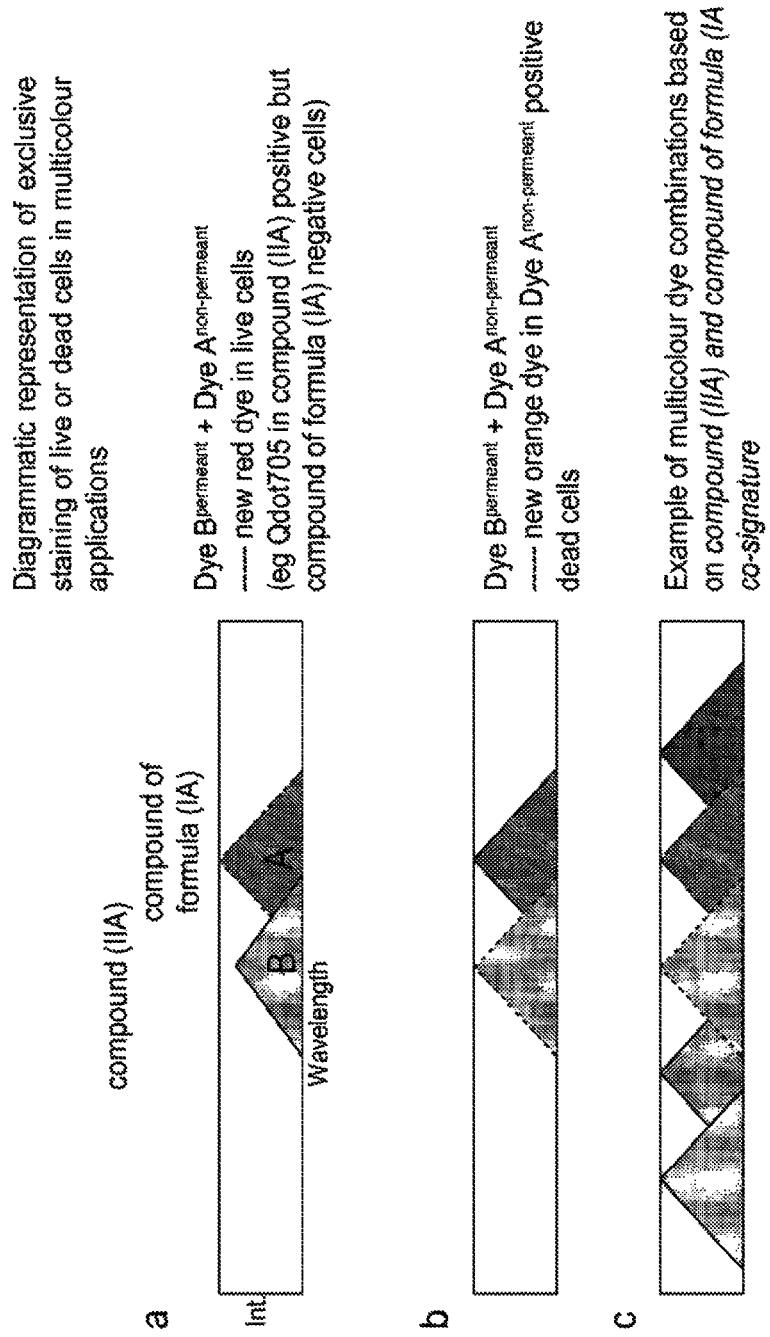
FIG. 3 is a diagram of fluorescence spectra for various multi-colour dye combinations based on a cell permeant/cell impermeant dye combination of the invention, in particular (a) shows a three parameter, two colour detection scheme in live cells (b) shows a three parameter, two colour detection scheme for dead cells and (c) shows a multi-colour detection scheme.

The invention provides a means of labelling live cells and dead cells using a combination of a permeant dye and an impermeant dye. This combination of dyes can be substantially mutually exclusive. In the sense that, detection of the permeant dye can be associated with the presence of live cells, and the detection of the cell impermeant dye can be associated with the presence of dead cells. This principle is shown in Table 1 below:

TABLE 1

Positive labelling of live/dead cells through detection of cell permeant/cell impermeant dyes.

| Cell state | Dye B$^{permeant}$ | Dye A$^{non-permeant}$ |
|---|---|---|
| live | + | − |
| dead | − | + |

Thus, the invention provides the capability to associate a live cell with fluorescence from the cell permeant dye, and to associate a dead cell with fluorescence from the cell impermeant dye, since there is little or no "cross channel" interference between the dyes. It will be appreciated that this provides the opportunity to perform numerous advantageous two-colour, two-fluorochrome experiments. Moreover, the present inventors have realised that dye combinations of this type also provide a platform for performing a range of advantageous experiments using one or more further fluorochromes. Table 2 shows without limitation examples of detection systems of this type with reference to the specific cell permeant/cell impermeant dye combination of compound of Formula (IIA)/compound of Formula (IA).

TABLE 2

Examples of fluorescent probes that can be used with a cell permeant/cell impermeant dye combination and predicted positive or negative staining patterns.

| Cell State | Combination staining patterns | | Inclusion of fluors with overlapping spectral properties | Inclusion of fluors with different spectral properties | | |
|---|---|---|---|---|---|---|
| | | | Red Probe for an analyte in intact cells (eg Qdot 705 nm emitting nano-particle labelled cell) | Orange probe for an analyte in non-intact cells (eg an Alexa 568 dye-tagged antibody for a disrupted cell membrane feature) | Green probe for inact cells (eg Annexin V-FITC) | Other fluors spectrally distinct for the analysis, for example of cell surface analytes |
| determined by a compound (IA) combined with a compound of formula (IIA) analysis | Compound of formula (IIA) (at 530 nm) staining | Compound (IA) Far red (at >695 nm) staining | | | | |
| Live cell stain | + | − | + | − | + or − | + or − |
| Dead cell stain | − | + | − | + | + or − | + or − |

These possible detection systems and others will now fee described in more detail with reference to FIGS. 1 to 9. FIG. 1 shows in general terms (ie, diagrammatically) the excitation and fluorescence spectra of Compound of Formula (IIA) (B) (Ex/Em peak at 518/615 nm); and a compound of Formula (IA) (A) (Ex/Em peak at 620/660 nm). Therefore, the Compound of Formula (IIA) fluorescence is generally in the orange portion of the visible spectrum, whereas compound (IA) fluorescence is generally in the far red portion of the visible spectrum, FIG. 1b shows the fluorescence spectrum of Compound of Formula (IIA) alone. The compound of Formula (IIA) is a cell permeant dye, and therefore it would be expected that the fluorescence signature B would be in connection with live or dead cells. FIG. 1c shows the fluorescence signature A of compound (IA) alone. Compound (IA) is a cell impermeant dye, and therefore the fluorescence signature A would only be observed in connection with dead cells or dying and not live cells. FIG. 2a shows the fluorescence obtained when a certain combination of a cell permeant dye (such as a compound of Formula (IIA)) and a cell impermeant dye (such as compound (IA)) is used in conjunction with live cells. As might perhaps be expected, it is only the fluorescence signature B associated with the cell permeant dye which is observed. FIG. 2b shows an entirely surprising effect provided by the present invention when certain combinations of cell permeant/cell impermeant dyes such as the compound of Formula (IIA)/compound (IA) combinations are used. It might be expected that a significant contribution of the observed fluorescence would emanate from the compound of Formula (IIA) dye. However, it has been found that with dead cells, little or no fluorescence is observed from the compound of Formula (IIA) dye. Rather, all or virtually all of the observed fluorescence is due to the cell impermeant dye, compound (IA). Therefore, the compound (IA) dye appears to quench the compound of Formula (IIA) signal. Very surprisingly, this quenching of the compound of Formula (IIA) signal appears to occur across the whole of the cell, and not just in the cell nucleus. Without wishing to be bound by any particular theory, it is believed that the surprising quenching effect provided by the invention may be due to the cell impermeant dye having a binding affinity for nucleic acid, and, possibly, other macromolecular material in the dead cells, which is higher than that of the cell impermeant dye. However, other mechanisms may play a role. The upshot is that it is possible to provide a "traffic light" system to indicate the state of a cell, wherein fluorescence in one spectral region A is associated with dead cells, and fluorescence in another spectral region B is associated with live cells.

One useful consequence of this system is that it is possible to provide a third defection channel using two colour defection in the spectral regions A and B, FIG. 3 shows some examples of how a three channel, two colour detection system might be provided with reference to the specific cell permeant/cell impermeant dye combination compound of Formula (IIA)/compound (IA). FIG. 3a shows fluorescence detected in live cells using the spectral ranges A and B. Fluorescence in the range B is associated with emission from the compound of Formula (IIA) as before. In this scheme, compound of Formula (IIA) is used in combination with compound (IA) and a further red dye or light emitting agent preferably associated with intact cells such as Qdot 705 nm emitting nanocrystals. This system exploits the fact that cells which provide a positive compound of Formula (IIA) signal do not exhibit a signal in the red due to compound (IA), and can be positively identified as live cells. The invention comprehends that live cells which have been "tagged" in this way through compound of Formula (IIA) fluorescence in the orange have a potential detection channel in the red region A which is free from interference from compound (IA) emission. FIG. 3b depicts a detection scheme which exploits the existence of a potential detection channel in dead cells in the orange region B which is substantially free from interference from compound of Formula (IIA) fluorescence. As shown in FIG. 3b, the presence of compound (IA) fluorescence in the red spectral region A effectively "tags" a cell as a dead cell. If a second orange dye is used, then a fluorescence spectrum such as that shown in FIG. 3b can be obtained, wherein the second orange dye can be used to provide further information about dead cells. It is extremely convenient to utilise three fluorochrome, two colour detection systems of this type, since a large amount of information can be extracted using a relatively simple detection system. However, the invention includes the use of multi colour dye combinations utilising fluorescence in more than two regions of the electromagnetic spectrum. FIG. 3c depicts a generalised multi colour dye fluorescence scheme, wherein one or more dyes which fluoresce in spectral regions differing from the spectral regions A and B are used.

Figure 4:
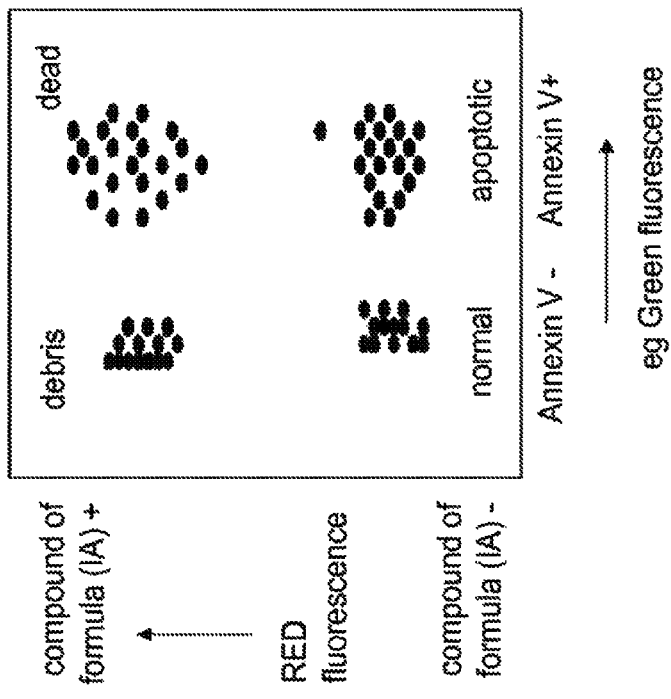
FIG. 4 is a diagram of fluorescence obtained from a detection system using a compound of Formula (IA) and Annexin V combination.

FIG. 4 shows results which might be obtained from a detection system which utilises compound (IA) in combination with an Annexin V assay such as AnnexinV-FITC which fluoresces in the green spectral region. This combination of dyes provides enhanced discrimination of the stages of cell death connected with apoptosis. As shown in FIG. 4, a low compound (IA)/low Annexin V signal is indicative of normal cells. Apoptotic cells are indicated by an increased Annexin V signal in combination with a low compound (IA) signal. The onset of cell death is indicated by the presence of both a high Annexin V signal and a restricted compound (IA) signal. Additional discrimination is provided by a channel comprising a low Annexin V signal and a high compound (IA) signal which is indicative of cellular debris.

FIG. 5 is a plot of the same general type as that shown in FIG. 4, which in this instance shows fluorescence intensify in a detection system which utilises the compound of Formula (IIA)/compound (IA) dye combination. Again, a level of the discrimination is observed in the progression of cells through to cell death. More specifically, when a low compound (IA) fluorescence signal is reported, three distinct "channels" can be identified. A positive signal in the orange for compound of formula (IIA) in combination with a low compound (IA) signal is indicative of normal cells, whereas an enhanced compound of Formula (IIA) signal is indicative of arrested cells. Note that a negative signal for both compound (IA) and compound of Formula (IIA) is indicative of cellular debris. A positive compound (IA) signal in combination with a negative compound of Formula (IIA) signal is indicative of dead cells. The skilled reader will appreciate from a consideration of FIG. 5 that there are potentially two further channels available, i.e., the combination of a high red signal with either a high orange or an enhanced orange signal. Since the high or enhanced orange signal is associated with the presence of live cells, it is not possible to obtain a high compound (IA) signal in combination with these orange signals. Instead, it is possible to utilise a third fluorochrome which fluoresces in the red region, such as Qdot 705 nm emitting nanocrystals, to provide a two colour, three fluorochrome analysis system. An advantage with such a system is that a single laser colour may fee used to excite all three fluorochromes, for example using 488 nm radiation from an Ar-ion laser.

FIG. 6 is a plot of the same general type as that shown in FIG. 6, which depicts a two colour, three fluorochrome analysis system using Qdot 705 nm emitting nanocrystals in combination with compound (IA) and compound of Formula (IIA). It can be seen that fluorescence in the red spectral region from the Qdot nanocrystals is observed in the two channels which are made available owing to the absence of compound (IA) fluorescence from live cells.

Figure 7:
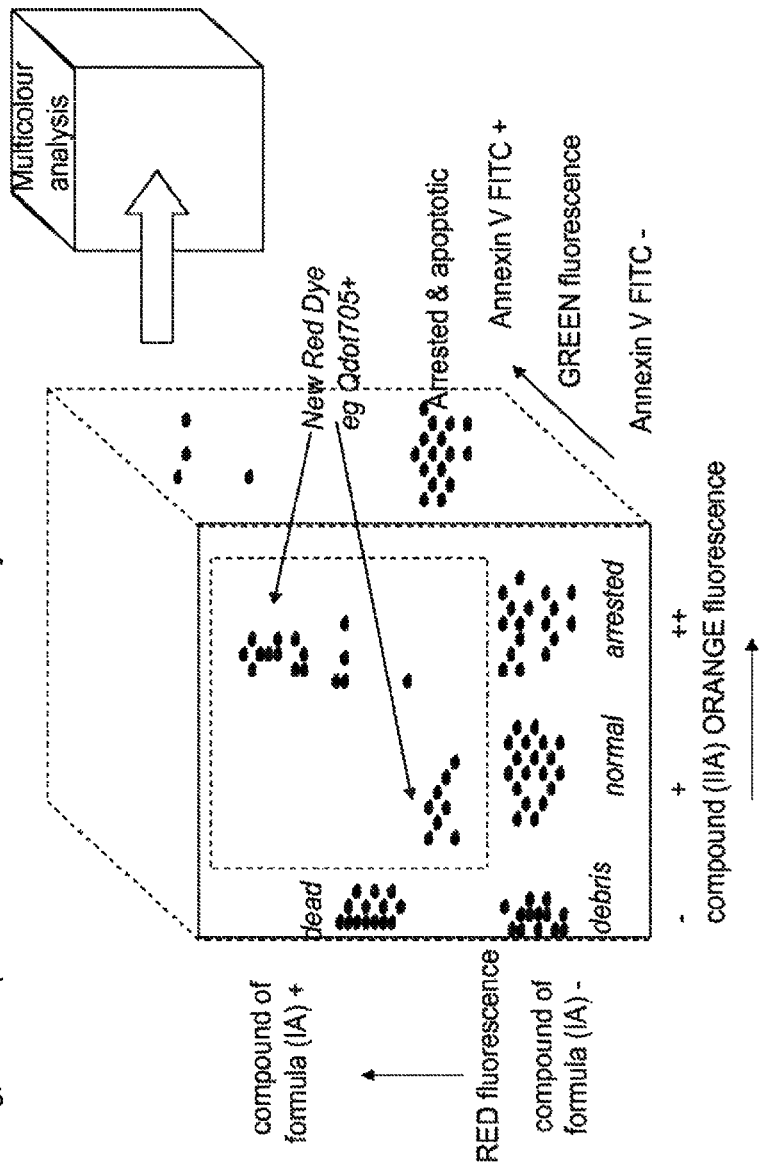
FIG. 7 is a diagram of fluorescence obtained from a three colour four fluorochrome detection system.

FIG. 7 shows results which can be obtained from a three colour system which is based on the compound of Formula (IIA)/compound (IA) cell permeant/cell impermeant dye combination. In this embodiment, a third fluorochrome such as Qdot705 nm emitting nanocrystals which fluoresce in the red region of the spectrum is used in order to probe live cells which have been positively labelled through the defection of compound of Formula (IIA) fluorescence. Additionally, a fourth fluorochrome such as AnnexinV-FITC is also used, with detection being made in the green region of the spectrum. This detection arrangement might be characterised as a two laser three colour four fluorochrome analysis technique. As shown in FIG. 7, the result which might be obtained from such a system can be presented using a three axis system to represent the fluorescence obtained in the three colour ranges. Therefore, the results obtained can be understood in terms of a three dimensional volume of data, which provides an enhanced level of discrimination in the progression of cells from normal state through apoptosis and cell death. In particular, the combination of low compound (IA) signal, enhanced compound of Formula (IIA) signal and high Annexin V-FITC signal is indicative of cells which are both arrested and apoptotic, whereas the combination of high compound (IA) signal, low compound of Formula (IIA) signal and high Annexin V-FITC signal is indicative of dead cells. It can be seen that this system can provide a great deal of information on cellular processes. It should be noted that all cells are present in the detection volume depicted in FIG. 7. A suitable multi-colour analysis can be performed in order to interpret the results. Other combinations of fluorochromes might be used in order to provide different or further levels of discrimination and information. In principle, further fluorochromes still might be utilised in order to provide further information. A further fluorochrome might fluoresce in a different spectral or region to provide an additional colour channel, or, possibly, a fluorochrome which fluoresces in the orange or green spectral regions might be used provided that the detection characteristics of such an additional fluorochrome do not interfere with the compound of Formula (IIA) or AnnexinV-FITC detection channels. Green and/or cyan dyes may be used in order to track cell change processes.

EXAMPLE 1. SYNTHESIS OF COMPOUND OF FORMULA (IIA) [1,5-BIS{[2-(DIMETHYL-AMINO)ETHYL]AMINO}ANTHRACENE-9,10-DIONE] AND A COMPOUND OF FORMULA (IB) [1,5-BIS{N-[2-(TRIMETHYLAMINO)ETHYL]AMINO}ANTHRACENE-9,10-DIONE IODIDE]

[1,5-Bis{N-[2-(dimethylamino)ethyl]amino}anthracene-9,10-dione was synthesised according to Example 1 of WO39/85992. Chloroform (2 mL) was added to 1,5-Bis{(2-(dimethylamino)ethyl]amino}anthracene-9,10-dione (58 mg, 0.152 mmol). To the dark purple solution was added MeCN (1 mL) followed by methyl iodide (95 µl, 1.524 mmol). After stirring for 10 mins, a precipitate forms. After stirring for 4 hrs, the volatiles were evaporated. The residue was triturated from chloroform (5 ml), collected by filtration was washed with dichloromethane (20 ml) and diethylether (10 ml). A dark pink solid was isolated (0.09 g, 0.135 mmol, 89% yield). $^1$H NMR (400 MHZ, $d_6$-DMSO) δ: 9.69 (2H, t), 7.72 (2H, dd), 7.52 (2H, dd), 7.30 (2H, dd), 3.91 (4H, q), 3.62 (4H, t), 3.18 (18H, s)

EXAMPLE 2. SYNTHESIS A COMPOUND OF FORMULA (IA) [1,5-BIS{[2-(TRIMETHYL-AMINO)ETHYL]AMINO}-5,8-DIHYDROXYAN-THRACENE-9,10-DIONE IODIDE]

1,5-Bis{[2-(dimethylamino)ethyl]amino}-5,8-dihydroxy-anthracene-9,10-dione was synthesized according to Example 1 of WO99/65992. Chloroform (2 mL) was added to 1,5-Bis{[2-(dimethylamino)ethyl]amino}-5,8-dihydroxy-anthracene-9,10-dione (44 mg, 0.107 mmol). To the dark purple solution was added MeCN (2 ml) followed by methyl iodide (66.6 µl, 1.067 mmol). After stirring for 1 min a precipitate forms. After stirring for 4 hrs, the volatiles were evaporated. The residue was triturated from chloroform (5 ml), collected by filtration was washed with dichloromethane (20 ml) and diethylether (10 ml). A dark blue solid was isolated. Yield=173-012 (0.05 g, 0.068 mmol, 63.9% yield) $^1$H NMR (400 MHz, $d_6$-DMSO) δ: 13.97 (2H, s), 9.77 (2H, br t), 7.49 (2H, d), 7.40 (2H, d), 3.98 (4H, br q), 4.09 (4H, t), 3.19 (18H, s).

EXAMPLE 3 SPECTRAL PROPERTIES OF COMPOUND (IA)

Compound (IA) was synthesized using the principles described in Example 2 and stored at +4° C. as a stock solution of 5 mM compound (IA) dilution in buffer. Absorbance spectra were obtained using a spectrometer and a 20 µM solution of agent dissolved in PSS and measured in a 1 cm path quartz silica cuvette. Fluorescence spectra for a solution of 20 µM compound (IA) in a 1 cm path length semi-micro quartz cuvette were determined by excitation at 633, 589, 534, 488 nm. Fluorescence measurements were made on a Parkin Elmer LS50 spectrofluorometer with slit widths set at 10 nm. The spectrofluorometer was equipped with a red-sensitive photomultiplier tube (Type R928; Hamamatsu Photonics KK, Japan. Data were accumulated and exported into a spread sheet to correct for the buffer control and to determine emission maxima. The results are shown in FIG. 8. Compound (IA) may be sub-optimally excited by wavelengths from 488 nm (in flow cytometry) and up to 647 nm (Ex$\lambda$max 846 nm). Typically, for cell imaging, excitation is performed with either 833 nm or 647 nm wavelengths. Emission spectra are independent of excitation wavelength, ie, all the emission spectra are identical irrespective of excitation wavelength.

EXAMPLE 4 APPLICATION OF CELL IMPERMEANT PROPERTIES OF COMPOUND (IA) IN DISTINGUISHING BETWEEN LIVE AND DEAD CELLS IN AN ANNEXINV ASSAY FOR THE INDUCTION OF CELL DEATH

This example relates to later stage cell death associated with the translocation of phosphatidylserine molecules from the inner (cytoplasmic) leaflet of the plasma membrane in human B cell lymphoma (DoHH2) cells that have been exposed to a cytotoxic drug (VP-18). Detection of dose-dependent induction of apoptosis was performed using flow cytometry.

We have sought to demonstrate the application of compound (IA) as a cell viability marker determining the non-viable fraction due to cell enhanced membrane permeability as a result of induced apoptosis with an etoposide (VP-16) including the spectral advantages of using a deep-red fluorescent probe from that of other commonly used fluorochromes by using selective excitation.

Compound IA was able to detect with similar accuracy as propidium iodide the non-viable fraction. This fraction showed a dose dependent increase upon increased doses of etoposide. Timed uptakes were done to optimise compound (IA) labelling. Dose modification was also performed to determine optimal concentration of compound (IA).

Reagents

VP-18 (VP-18-213; VEPESID; Etoposide) was provided as a 34 mM stock solution (Bristol Meyers Pharmaceuticals, Syracuse, N.Y.) and stored at 4° C. Fluorescein-conjugated annexin V (annexin V-FITC) was purchased from Pharmingen (Becton Dickinson UK, Oxford, UK.), Propidium iodide (PI) was obtained as a 1 mg/ml solution in $H_2O$ (Molecular Probes Europe, Leiden, The Netherlands). Compound (IA) was formulated in water as a 5 mM solution and stored at 4° C.

Cell Culture and Drug Treatment:

The human follicular B-lymphoma cell lines were used in this study. DoHH2 was a kind gift from Dr J C Kluin-Nelemans [Leiden, The Netherlands], DoHH2 was routinely maintained in RPMI 1640 supplemented with 5% FCS and 100 U ml-1 penicillin, 100 µg ml-1 streptomycin, and 2 mM glutamine. The cells were passaged twice weekly at an initiating density of 5×104 cells ml-1 cultured at 37° C. in a humidified atmosphere of 5% CO2/95% air. Cells were exposed to a range of VP-16 doses (0-2.5 µM) to induce apoptosis [Paul J. Smith, Marie Wiltshire, Sharon Davies, Suet-Feung Chin, Anthony K. Campbell, and Rachel J. Errington (2002). DNA damage-induced [Zn2+]i transients: correlation with cell cycle arrest and apoptosis in lymphoma cells. Am J Physiol Cell Physiol 283 (2): 609-622], Human Jurkat cells were cultured in a similar manner.

Sample Preparation for Annexin-V Labelling;

Samples were prepared for the detection of Annexin V-FITC surface binding to cells undergoing apoptotic changes and co-stained with PI or the compound (IA) to detect loss of plasma, membrane integrity. Samples were prepared according to Vermes et al. Briefly, cell samples (4×10$^5$ cells/ml) were washed with cold PBS and resuspended in 1× binding buffer (10 mM Hepes/NaOH, pH 7.4, 140 mM NaCl, 2.5 mM $CaCl_2$) at a concentration of 2×10$^5$ cells/ml. 100 µl of this solution was transferred to a polystyrene round bottomed flow tube (Falcon) per sample to which 5 µl of Annexin V-FITC and 10 µl PI (50 µg/ml stock) was added as required. Control samples were sham-treated as necessary. Samples were gently vortexed, then incubated in the dark for 15 min at room temperature. 400 µl of 1× binding buffer was added to each tube and samples held on ice for a maximum of 1 hour prior to analysis by flow cytometry.

Flow Cytometry:

A FACS Vantage flow cytometer (Becton Dickinson Immunocytometry Systems, San Jose, Calif.) equipped with a Coherent Enterprise II argon ion laser having 438 nm and multiline UV (351-355 nm) outputs (Coherent, Inc., Santa Clara, Calif.) was used. The Enterprise II laser power was regulated at 30 mW (monitored on the multiline UV output) CELLQuest software (Becton Dickinson Immunocytometry Systems) was used for signal acquisition and analysis. Forward scatter (FSC) and side scatter (SSC) were acquired in linear mode. FITC and PI fluorescent signals derived from 488 nm excitation were detected in logarithmic mode at photomultipliers detecting emissions spectrally selected by optical filters; compound (IA) signal derived from 488 nm excitation was detected in logarithmic or linear mode but could also be detected following excitation at 633 nm using a third laser conveniently incorporated into the optical system. Compound of Formula (IIA) signal derived from excitation at 488 nm was detected in both logarithmic or linear mode. Signals for forward and side scatter and fluorescence were collected for 10,000 cells using the forward light scatter parameter as the master signal. Pulse analysis of fluorescence signals and fluorescence compensation settings were modified to improve recognition of cell subsets in multi-fluor combinations as readily understood in the art. Data are expressed as mean fluorescence intensity (FI) values and are shown in FIG. 9.

EXAMPLE 5 PROMINENT NUCLEAR STAINING OF FIXED U-2 OS HUMAN OSTEOSARCOMA CELLS BY A COMPOUND OF FORMULA (IA) DETECTED BY FLUORESCENCE MICROSCOPY

We have sought the property of compound (IA) to effectively target nuclear DNA.

Cell culture: Human osteosarcoma cells U-2 OS (ATCC HTB-96) cells (adherent) were cultured in McCoy's 5a medium supplemented with 10% foetal calf serum (PCS), 1 mM glutamine, and antibiotics and incubated at 37° C. in an atmosphere of 6% $CO_2$ in air. For fluorescence imaging experiments, cells were grown at a density of 1×10$^5$ cells ml$^{-1}$ as a monolayer in coverglass bottomed chambers (Nunc, 2 Well Lab-Tek II, Fisher Scientific).

Imaging: Following a 24 hour period cells were then fixed with 4% paraformaldehyde in PBS for 15-30 min at room temperature. No washing step is required. Compound (IA) was used in a manner appropriate to being the final staining procedure, after any treatment. Compound (IA) was added directly at 20 μM in to a 0.5 ml PBS overlay of the adherent cells. Cells were directly viewed using wide-field fluorescence microscopy. Chambers were placed onto an Axiovert 100 microscope (Carl Zeiss, Welwyn Garden City, UK and using a 40×, 1.3 NA oil immersion plan apochromat lens) fluorescence images (Ex: 620/60 nm; Em 700/75 nm) nm captured using an ORCA-ER CCD camera (Hamamatsu, Reading, UK) and MetaMorph (MDS, USA) acquisition software. Cells showed the localization of high levels of compound (IA) in the nucleus. The compound (IA) staining of nuclei were segmented using a simple threshold algorithm which depict the nuclei, and provide binary or mask information of each nucleus (object) localization. The original compound (IA) nuclear localisation and after segmentation are shown. Results are shown in FIG. 10.

EXAMPLE 6. THE STAINING OF CELLS WITH COMPROMISED MEMBRANES BY A COMPOUND OF FORMULA (IA) ALLOWS FOR THE IDENTIFICATION BY NEGATIVE STAINING OF INTACT CELLS

This example shows the analysis of cell death induction by staurosporine in populations of human Jurkat cells analysed by flow cytometry. We have sought to demonstrate the application of compound (IA) as a cell viability marker determining the non-viable fraction due to cell enhanced membrane permeability as a result of induced cell death with staurosporine.

Cell Culture and Drug Treatment:

A Jurkat cell line was used in this study Jurkat cultures was routinely maintained in RPMI 1840 supplemented with 10% PCS and 100 U ml-1 penicillin, 100 μg ml-1 streptomycin, and 2 mM glutamine. The cells were passaged twice weekly at an initiating density of $5 \times 10^4$ cells $ml^{-1}$ cultured at 37° C. in a humidified atmosphere of 5% CO2/95% air. Cells were set at $0.5 \times 10^5$ cells/ml, 5 ml per flask. Cells were exposed to 0 and 2 μM staurosporine for 24 hours under standard culture conditions to induce cell death. Compound (IA) (3 μM) from a 5 mM stock was added to each sample and analysed by flow cytometry.

Flow Cytometry:

A FACS Vantage flow cytometer (Becton Dickinson Immunocytometry Systems, San Jose, Calif.) equipped with a Coherent Enterprise II argon ion laser having 488 nm and multiline UV (361-355 nm) outputs (Coherent, Inc., Santa Clara, Calif.) was used. The Enterprise II laser power was regulated at 30 mW (monitored on the multiline UV output) CELLQuest software (Becton Dickinson Immunocytometry Systems) was used for signal acquisition and analysis. Forward scatter (FSC) and side scatter (SSC) were acquired in linear mode. Compound (IA) fluorescent signals derived from 488 nm excitation were detected in logarithmic mode at FL3 695LP Signals for forward and side scatter and fluorescence were collected for 10,000 cells using the forward light scatter parameter as the master signal. Data are displayed as contour plots fluorescence intensity (695LP) for compound (IA) against forward scatter signal to indicate cell size. Results are shown in FIG. 11.

EXAMPLE 7. THE EFFECT OF INCUBATION OF HUMAN B CELL LYMPHOMA (SU-DHL-4) CELLS WITH A COMPOUND OF FORMULA (IA) REVEALING THE LOW TOXICITY OF THE CELL IMPERMEANT DYE INDICATING AN ADVANTAGEOUS PROPERTY FOR INCORPORATION INTO LONG TERM FIVE CELL INCUBATION STUDIES FOR THE DETERMINATION OF THE ACCRUAL OF CELL DEATH ASSOCIATED WITH A GIVEN TREATMENT

Cell Culture and Treatment:

A human follicular 8-lymphoma cell lines were used in this study. SU-DHL-4 was routinely maintained in RPMI 1640 supplemented with 10% FCS and 100 U ml-1 penicillin, 100 $μgml^{-1}$ streptomycin, and 2 mM glutamine. The cells were passaged twice weekly at an initiating density of $5 \times 10^4$ cells $ml^{-1}$ cultured at 37° C. in a humidified atmosphere of 6% $CO_2$/95% air. Cells were set at $0.5 \times 10^5$ cells/ml at 5 ml per flask. Each culture was continuously exposed to one of three compound (IA) closes (0, 3 and 10 μM) for 96 hours under standard culture conditions. At time (t) 0, 24, 48, 72 and 96 hours cell density was determined by Coulter counting of 0.4 ml samples from each flask. Data are displayed as increase in relative cell number (Nt/N0) (695LP) against time (hours) for the given concentration of compound (IA). The results are shown in FIG. 12.

EXAMPLE 8. EARLY STAGE IN HUMAN JURKAT CELL DEATH ASSOCIATED WITH THE LOSS OF MITOCHONDRIAL MEMBRANE POTENTIAL IN RESPONSE TO THE APOPTOSIS INDUCING AGENT STAUROSPORINE

The incorporation of a preferred cell impermeant dye (compound of Formula (IA)) into typical multi-parameter analyses using other fluorescent reagents with properties of interest in reporting the loss of cellular integrity with advantages for the co-incorporation into assays to provide a means of distinguishing intact and damaged cells.

In this example, the dye JC-1 (5, 5', 6, 6'-tetrachloro-1, 1', 3, 3'-tetraethylbenzimidazol-carbocyanine iodide) is a lipophilic fluorescent cation that incorporates into the mitochondrial membrane, where it can form aggregates due to the physiological maintenance membrane potential of mitochondria. Aggregation modifies the fluorescence properties of JC-1 leading to a shift from green to orange fluorescence. Flow cytometry or imaging was used to monitor the decrease of the orange fluorescence and an increase of the green fluorescence allowing apoptotic cells to be distinguished from non-apoptotic cells. Here the further incorporation of the preferred cell impermeant dye with red but not orange fluorescence properties allows for the co-identification of those cells already in late stages of cell death associated with loss of membrane integrity providing a finer resolution of the stages of cell death not previously attainable.

Cell Culture and Drug Treatment:

A Jurkat cell line was used in this study Jurkat cultures was routinely maintained in RPMI 1640 supplemented with 10% PCS and 100 U ml-1 penicillin, 100 μg ml-1 streptomycin, and 2 mM glutamine. The cells were passaged twice weekly at an initiating density of $5 \times 10^4$ cells $ml^{-1}$ cultured at 37° C. in a humidified atmosphere of 5% CO2/95% air. For the assay, cells were set at $0.5 \times 10^5$ cells/ml, 1 ml per well. Cells were exposed to 0 (control conditions) and 1 μM staurosporine for 4 hours. Cells were washed and exposed to JC-1 (RPM). Compound (IA) (3 μM) from a 5 mM stock was added to each sample. These were then analysed by flow cytometry or placed into a Nunc, 2 Well Lab-Tek II, (Fisher Scientific) and analysed by three channel confocal microscopy.

Multi-Parameter how Cytometry of Staurosporine Treated Cells

A FACS Vantage flow cytometer (as for example above). Forward scatter (FSC) and side scatter (SSC) were acquired in linear mode. JC-1 two parameter fluorescent signal were derived from 488 nm excitation were detected in logarithmic mode Green J-monomer was detected using FL1 (530/30 nm emission); Orange J-aggregate was detected using FL2 (585/42 nm emission). Compound (IA) fluorescent signals also derived from 488 nm excitation were detected in logarithmic mode at FL3 at 695LP. Signals for forward and side scatter and fluorescence were collected for 10,000 cells using the forward light scatter parameter as the master signal. Results shown in FIG. 13. (A-C). JC-1 data are displayed as contour plots fluorescence intensity (585/42 nm) for J-aggregate against fluorescence intensity (530/30 nm) for J-monomer. These are further segmented to derive the cells with high mitochondrial membrane potential (upper region) and cells with low mitochondrial potential (lower region). Cell viability is simultaneously depicted in these two fractions with compound (IA). The upper region consists of predominantly live cells and the lower region consists of both non-viable and live cells, compound (IA) functionality can depict these sub-fractions (early (compound (IA) negative) and late apoptosis (compound (IA) positive and permeable).

Multi-parameter imaging of staurosporine treated cells. The scanning unit was a BioRad Radiance MP system (BioRad Microscience, Hemel Hempstead, UK) linked to a Nikon Eclipse TE300 inverted microscope, using a planapo 60x/1.4 NA oil immersion lens. Three channel, three-dimensional (3D) (x,y,z) images were collected using a confocal configuration (pinhole closed). All channels green (J-monomer excitation at 488 nm emission at 500-530 nm); orange (J-aggregate excitation at 488 nm emission at 590/70; and red (compound (IA)) (non-viable cell marker excitation at 637 nm emission at 660LP) were collected simultaneously. The 3D image sequence were processed into single maximum projection images, and all three channels displayed as J-monomer, J-aggregate and DNA nucleus cells. Results are shown in FIG. 13 (D).

We have sought the exploitation of multi-fluorochome applications exploiting the concept of signal extinction by target competition between the preferred cell impermeant dye and a second preferred cell permeant dye. The spectral separation provides for exclusive signals arising from only one dye within any given cell and therefore allows for their simple integration into existing multi-fluorochome assays with higher levels of polychromatic analyses readily understood within the field.

EXAMPLE 9. COMBINATION TRACKING OF CALL STATUS. THE LABELING OF CELLULAR POPULATIONS WITH THE COMPOUND OF FORMULA (IA) PLUS COMPOUND (IIA) TO DEMONSTRATE NO CO-LABELLING OF SUB-POPULATIONS IN DOHH2 CULTURES TREATED WITH VP-16 TO DERIVE AN ASSAY ACCOUNTING FOR VIABLE/ARRESTED (COMPOUND (IIA) POSITIVE) AND DAMAGED (COMPOUND (IA) POSITIVE) CELLS

Cell Culture and Drug Treatment:

A human follicular B-lymphoma cell line was used in this study. DoHH2 was routinely maintained in RPMI 1840 supplemented with 5% FCS and 100 U ml-1 penicillin, 100 μgml$^{-1}$ streptomycin, and 2 mM glutamine. The cells were passaged twice weekly at an initiating density of $5 \times 10^4$ cells ml$^{-1}$ cultured at 37° C. in a humidified atmosphere of 5% $CO_2$/95% air. Cells were set at $5 \times 10^5$ cells/per ml and exposed to VP-16 doses (0.25 μM) to induce apoptosis, 20 μM Compound (IIA) and 4 μM compound (IA) were added to 1 ml of cells and incubated under standard culture conditions for 10 minutes. The samples were analysed by flow cytometry.

A FACS Vantage flow cytometer (as for example above) was used. Compound (IIA) and compound (IA) fluorescent signals derived from 488 nm excitation were defected in linear mode at FL2 for Compound (IIA) (585/42 nm filters); compound (IA) signal derived from 488 nm were detected in linear mode at FL3 with a 695LP filter and a FL 1/2 580 nm SP dichroic SP to determine scatter properties. Signals for forward and side scatter and fluorescence were collected for 10,000 cells using the forward light scatter parameter as the master signal. Data are expressed as contour plots and are shown in FIG. 14. Contour plots of side versus forward scatter depict two populations of cells. The addition of Compound (IIA) and compound (IA) provide functional status of these cultures. First, all cells are accounted in the assay using these two co-targetting fluorophores. Compound (IA) identifies the non-intact cell fraction, while the Compound (IIA) positive cells represent the live cell (viable) fraction. Note that this viable fraction has two populations further depicting an accrual of an arrested (G2) population. Further, the Compound (IIA) fraction represented a unique fraction with a higher forward scatter properties (ie cell size), while the compound (IA) population displayed lower mean forward scatter properties.

The invention claimed is:

1. A composition suitable for use as a fluorescent dye for analyzing cells or other biological materials, comprising a mixture of:

a fluorescent, cell-impermeant, compound of Formula (I)

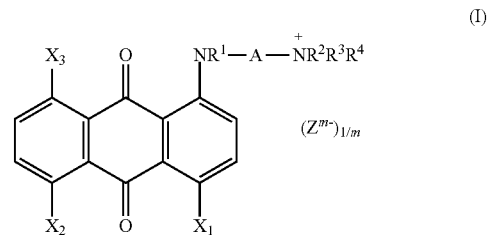

or a derivative in which the group NR' is quaternarized, wherein

A is a $C_{2-8}$ alkylene group;

R$^1$ selected from hydrogen, $C_{1-4}$ alkyl, and $C_{3-4}$ dihydroxyalkyl in which the carbon atom attached to the nitrogen atom does not carry a hydroxyl group and no carbon atom is substituted by two hydroxyl groups, and R$^2$, R$^3$, and R$^4$ are independently selected from $C_{1-4}$ alkyl, and $C_{3-4}$ dihydroxyalkyl in which the carbon atom attached to the nitrogen atom does not carry a hydroxyl group and no carbon atom is substituted by two hydroxyl groups, or R$^1$ is selected from hydrogen, $C_{1-4}$ alkyl, and $C_{3-4}$ dihydroxyalkyl in which the carbon atom attached to the nitrogen atom does not carry a hydroxyl group and no carbon atom is substituted by two hydroxyl groups, R$^4$ is selected from $C_{1-4}$ alkyl, and $C_{3-4}$ dihydroxyalkyl in which the carbon atom attached to the nitrogen atom does not carry a hydroxyl group and no carbon atom is substituted by two hydroxyl groups, and R$^2$ and R$^3$ together with the nitrogen atom to which R$^2$ and R$^3$ are attached form a heterocyclic ring, wherein the heterocyclic ring consists of a $C_{2-4}$ alkylene group together with the nitrogen atom;

$X_1$, $X_2$, and $X_3$ are independently selected from hydrogen, hydroxyl, NR$^1$-A-NR$^2$R$^3$R$^4$+(Z$^{m-}$) $_{1/m}$, halogeno amino, $C_{1-4}$ alkoxy, and $C_{2-8}$ alkanoyloxy; and (Z$^{m-}$) $_{1/m}$ is an anion of charge m, where m is 1, 2 or 3; together with at least a second fluorochrome or light-emitting compound, wherein the compound is cell permeant and is of Formula (II)

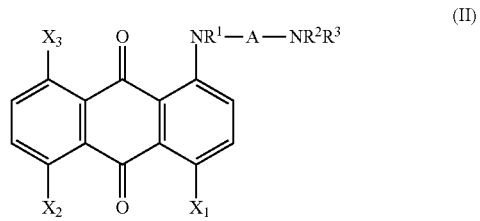

or an N-oxide thereof;
wherein
A is a $C_{2-8}$ alkylene group;
R$^1$, R$^2$, and R$^3$ are independently selected from hydrogen, $C_{1-4}$ alkyl, and $C_{3-4}$ dihydroxyalkyl in which the carbon atom attached to the nitrogen atom does not carry a hydroxyl group and no carbon atom is substituted by two hydroxyl groups, or R$^1$ is selected from hydrogen, $C_{1-4}$ alkyl, and $C_{3-4}$ dihydroxyalkyl in which the carbon atom attached to the nitrogen atom does not carry a hydroxyl group and no carbon atom is substituted by two hydroxyl groups, and R$^2$ and R$^3$ together with the nitrogen atom to which R$^2$ and R$^3$ are attached form a heterocyclic ring, wherein the heterocyclic ring consists of a $C_{2-6}$ alkylene group together with the nitrogen atom; and $X_1$, $X_2$, and $X_3$ are independently selected from hydrogen, hydroxyl, NR$^1$-A-NR$^2$R$^3$, halogeno amino, $C_{1-4}$ alkoxy, and $C_{2-8}$ alkanoyloxy;

said composition further comprising a first nucleic acid and a second nucleic acid, wherein the compound of Formula (I) forms a first fluorescent complex including the first nucleic acid, and the compound of Formula (II) forms a second fluorescent complex including the second nucleic acid, and the first fluorescent complex is formed in a non-intact cell and the second fluorescent complex is formed in an intact cell.

2. A composition according to claim 1 in which in Formula (I) at least one of $X_1$, $X_2$ and $X_3$ are NR$^1$-A-NR$^2$R$^3$R$^4$+(Z$^{m-}$)$_{1/m}$.

3. A composition according to claim 2 in which in Formula (I) $X_2$, but not $X_1$ and $X_3$ is NR$^1$-A-NR$^2$R$^3$R$^4$+(Z$^{m-}$)$_{1/m}$.

4. A composition according to claim 3 in which in Formula (I) $X_1$ and $X_3$ are both hydroxyl.

5. A composition according to claim 1 in which in Formula (I) $X_1$ and $X_3$ are both hydrogen.

6. A composition according to claim 1 in which in Formula (I) R$^1$ is hydrogen.

7. A composition according to claim 1 in which in Formula (I) R$^2$, R$^3$, and R$^4$ are Ci$_{1-4}$.

8. A composition according to claim 7 in which in Formula (I) R$^2$, R$^3$, and R$^4$ are methyl.

9. A composition according to claim 1 in which in Formula (I) A is (CH$_2$)$_2$.

10. A composition according to claim 1 in which the compound of Formula (I) is of Formula (IA).

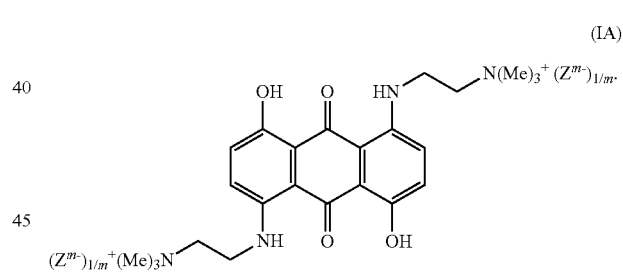

11. A composition according to claim 1 in which the compound of Formula (I) is of Formula (IB)

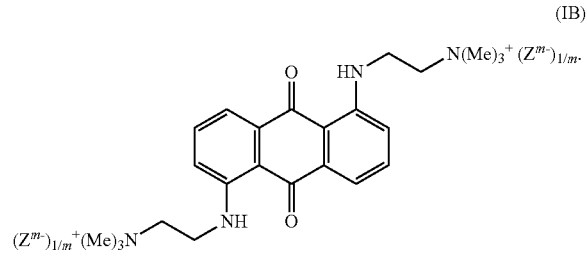

12. A composition according to claim 1 in which Formula (II) is a 1,5-amino substituted anthraquinone.

13. A composition according to claim 1 in which the

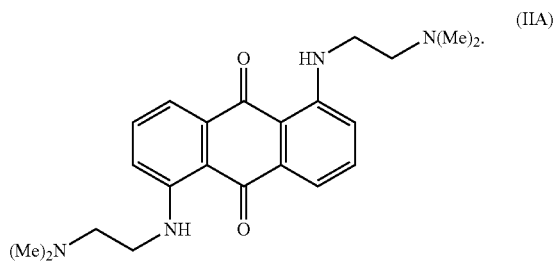
(IIA)

14. A composition, comprising a mixture of:
a compound of Formula (IA)

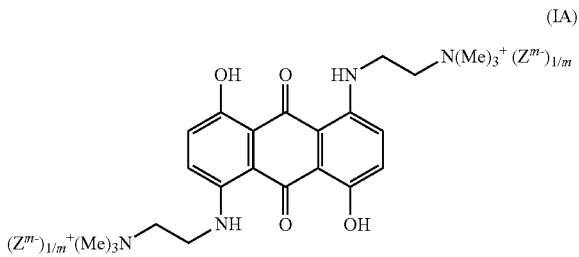
(IA)

where $(Z^{m-})$ is an anion of charge m, and where m is 1, 2 or 3;

together with
at least a second fluorochrome or light-emitting compound, wherein the compound is of Formula (IIA)

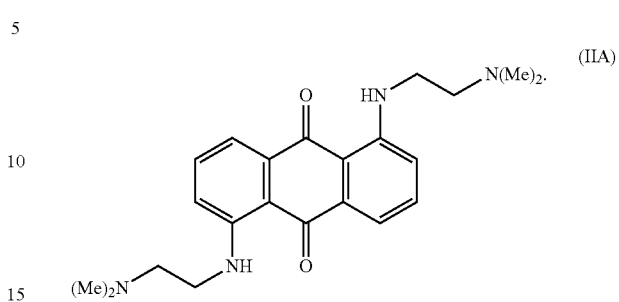
(IIA)

15. A composition according to claim 1 in which in Formula (I) $X_1$, $X_2$, and $X_3$ are independently selected from hydroxyl, $NR^1\text{-}A\text{-}NR^2R^3R^4{+}(Z^{m-})_{1/m}$, halogeno amino, $C_{1-4}$ alkoxy, and $C_{2-8}$ alkanoyloxy.

16. The composition of claim 14, further comprising a first nucleic acid and a second nucleic acid,
   wherein the compound of Formula (IA) forms a first fluorescent complex including the first nucleic acid, and the compound of Formula (IIA) forms a second fluorescent complex including the second nucleic acid.

17. The composition of claim 14, wherein the compound of Formula (IA) and the compound of Formula (IIA) are each present at a concentration of at most 5 mM.

* * * * *